United States Patent
Na et al.

(10) Patent No.: US 9,897,554 B2
(45) Date of Patent: Feb. 20, 2018

(54) METHOD OF INSPECTING SURFACE AND METHOD OF INSPECTING PHOTOMASK USING THE SAME

(71) Applicant: Samsung Electronics Co., Ltd., Suwon-si (KR)

(72) Inventors: Ji-hoon Na, Bucheon-si (KR); Dong-gun Lee, Hwaseong-si (KR); Byung-gook Kim, Seoul (KR); Rae-won Yi, Suwon-si (KR)

(73) Assignee: SAMSUNG ELECTRONICS CO., LTD., Yeongtong-gu, Suwon-si, Gyeonggi-do (KR)

( * ) Notice: Subject to any disclaimer, the term of this patent is extended or adjusted under 35 U.S.C. 154(b) by 0 days.

(21) Appl. No.: 15/093,770

(22) Filed: Apr. 8, 2016

(65) Prior Publication Data

US 2016/0356727 A1     Dec. 8, 2016

(30) Foreign Application Priority Data

Jun. 3, 2015  (KR) .................. 10-2015-0078666

(51) Int. Cl.
| | |
|---|---|
| *G01B 11/14* | (2006.01) |
| *G01N 21/956* | (2006.01) |
| *G01B 11/00* | (2006.01) |
| *G03F 1/84* | (2012.01) |

(52) U.S. Cl.
CPC .......... *G01N 21/956* (2013.01); *G01B 11/00* (2013.01); *G03F 1/84* (2013.01); *G01N 2021/95676* (2013.01); *G01N 2201/103* (2013.01)

(58) Field of Classification Search
CPC ......... G01B 11/00; G01N 2021/95676; G01N 21/956; G01N 2201/103; G03F 1/84; H01L 22/12; H01L 22/20
USPC ..... 356/625–640, 237.1–237.6, 239.1–239.8
See application file for complete search history.

(56) References Cited

U.S. PATENT DOCUMENTS

| | | |
|---|---|---|
| 6,978,215 B2 | 12/2005 | Nikitin |
| 7,288,764 B2 | 10/2007 | Sasajima et al. |
| 7,433,542 B2 | 10/2008 | Takane et al. |
| 7,663,103 B2 | 2/2010 | Kuribara et al. |
| 7,947,951 B2 | 5/2011 | Khursheed |
| 8,039,813 B2 | 10/2011 | Casares et al. |
| 8,213,722 B2 | 7/2012 | Kim et al. |
| 8,618,500 B2 | 12/2013 | Adamec |
| 8,637,834 B2 | 1/2014 | Knippelmeyer et al. |

(Continued)

FOREIGN PATENT DOCUMENTS

KR  10-2010-0134441   12/2010

OTHER PUBLICATIONS

Keeler et al, "High Throughput Data Acquisition With a Multi-Beam SEM." Proc. of SPIE vol. 9236, 92360B • © 2014 SPIE.

*Primary Examiner* — Tri T Ton
(74) *Attorney, Agent, or Firm* — Muir Patent Law, PLLC

(57) ABSTRACT

A method of inspecting a surface includes loading an inspection object on a stage of a multibeam inspection device configured to generate a beam array, and scanning a plurality of inspection areas of the inspection object at a same time with the beam array, wherein one of the first inspection areas is smaller than an area formed by a quadrangle connecting respective centers of corresponding four adjacent beams of the beam array, and an adjacent area of the one first inspection area is not scanned with the beam array.

20 Claims, 42 Drawing Sheets

(56) References Cited

U.S. PATENT DOCUMENTS

| | | | |
|---|---|---|---|
| 2005/0213086 A1* | 9/2005 | Hamamatsu | G01N 21/956 356/237.2 |
| 2008/0100843 A1* | 5/2008 | Kono | G01N 21/8806 356/369 |
| 2009/0114818 A1 | 5/2009 | Casares et al. | |
| 2010/0320382 A1 | 12/2010 | Almogy et al. | |
| 2015/0021474 A1 | 1/2015 | Firnkes et al. | |
| 2016/0003613 A1* | 1/2016 | Atiya | G01B 11/25 356/612 |

* cited by examiner

METHOD OF INSPECTING SURFACE AND METHOD OF INSPECTING PHOTOMASK USING THE SAME

CROSS-REFERENCE TO RELATED APPLICATION

This application claims the benefit of priority under 35 U.S.C. § 119 to Korean Patent Application No. 10-2015-0078666, filed on Jun. 3, 2015, in the Korean Intellectual Property Office, the disclosure of which is incorporated herein by reference in its entirety.

BACKGROUND

The present disclosure relates to a method of inspecting a surface and a method of inspecting a photomask. The present disclosure also relates to a method of inspecting a surface using a multibeam inspection device and a method of inspecting a photomask using a multibeam inspection device.

According to an accelerating trend of high integration of semiconductor devices, the importance of critical dimension uniformity (CDU) of light shielding patterns in a photomask has increased. However, since the number of inspection points where an actual measurement of a critical dimension (CD) is performed is extremely limited due to time constraints, it may be difficult to predict the CDU of the light shielding patterns in the photomask. Accordingly, it will be beneficial to improve the inspecting method of the CDU of light shielding patterns in a photomask.

Furthermore, a method of precisely inspecting the uniformity of a pattern and a thickness, and inspecting a defect rate of various foil surfaces used to manufacture a semiconductor device at high speed is also beneficial.

SUMMARY

Aspects of the disclosed embodiments provide a method of precisely inspecting, at a plurality of inspection points and at high speed, critical dimension uniformity (CDU) by measuring a pattern, a thickness, and a defect rate of various foil surfaces or a critical dimension (CD) of light shielding patterns in a photomask.

According to an aspect of the inventive concept, there is provided a method of inspecting a surface, the method including loading of an inspection object on a stage of a multibeam inspection device configured to generate a beam array, setting of a plurality of beams in the beam array to respectively have coverage regions defined by respective pitches between the beams, and setting field of views (FOVs) of the beams to be respectively smaller than the coverage regions, scanning, with the beam array, of a plurality of inspection points on the inspection object, the inspection points corresponding to the set FOVs.

In some embodiments, the scanning may be performed while the stage that supports the inspection object is moving, and the beam array may be redirected along the inspection points on the inspection object moving with the stage.

In some embodiments, the inspection object may have a plurality of unit regions corresponding to the beam array, and the beam array may be redirected from inspection points of one unit region to inspection points of another unit region.

In some embodiments, the inspection points in the one unit region and the inspection points of the other unit region may not overlap each other.

In some embodiments, the FOV of each of the beams may be smaller than or equal to an area obtained by equally dividing the coverage region by the number of the beams in the same direction as a stage moving direction.

In some embodiments, a region of the inspection object corresponding to the coverage region of one of the beams may be equally divided into a plurality of sub-regions, and each of the sub-regions may be scanned by each of the beams in the same direction as the stage moving direction.

In some embodiments, a redirection distance of the beam array may be in a range from a pitch between adjacent beams to a sum of pitches between the beams in a same direction as the stage moving direction.

In some embodiments, at least one of the inspection points in the one unit region and at least one of the inspection points of the other unit region may overlap.

In some embodiments, the method may further include obtaining of a representative image by averaging images obtained by scanning the inspection points a plurality of times.

In some embodiments, a redirection distance of the beam array may be substantially the same as each of the pitches between the beams.

In some embodiments, the scanning may further include scanning of the inspection points on the inspection object a plurality of times and obtaining of a representative image by averaging obtained by scanning the inspection points a plurality of times.

In some embodiments, the scanning may cover a whole area of the inspection object.

In some embodiments, the inspection object may be a photomask including light shielding patterns.

In some embodiments, the method may further include measuring of a CD of the light shielding patterns from the images obtained by the scanning of the inspection points.

According to an aspect of the inventive concept, there is provided a method of inspecting a surface including: loading of an inspection object on a stage of a multibeam inspection device configured to generate a beam array, scanning, with the beam array, inspection points of one unit region while the stage is moving, wherein the inspection object includes a plurality of the unit regions corresponding to the beam array, and redirecting the beam array from the inspection points in the one unit region to the inspection points of another unit region.

In some embodiments, a redirection distance of the beam array may be substantially equal to a pitch between the beams in the beam array or a sum of pitches between the beams in the same direction as the stage moving direction.

In some embodiments, the scanning may further include scanning of the inspection points on the inspection object a plurality of times by at least one of the beams in the beam array and obtaining a representative image by averaging images obtained by scanning the inspection points a plurality of times.

In some embodiments, the inspection points in the unit regions may be separated from each other with fixed intervals.

According to another aspect of the inventive concept, there is provided an inspection method of a photomask including: loading of a photomask on a stage of a multibeam inspection device configured to generate a plurality of beams, setting of each of the beams to respectively have a coverage region defined by respective pitches between the beams, and setting respective FOVs of the beams to be smaller than the coverage region, scanning first inspection points of the photomask with the beams, the inspection points corresponding to the FOVs, while the stage is moving with the photomask supported thereon, and redirecting the beams to second inspection points of the photomask after the scanning of the first inspection points is completed, the second inspection points corresponding to the FOVs.

In some embodiments, a redirection distance of the beam array may be substantially equal to a pitch between the beams in the beam array or a sum of pitches between the beams in the same direction as the stage moving direction.

According to some embodiments, a method of inspecting a surface comprises loading an inspection object on a stage of an inspection device generating a beam array and scanning a plurality of first inspection areas of the inspection object at a same time with the beam array, wherein one of the first inspection areas is smaller than an area formed by a quadrangle connecting respective centers of corresponding four adjacent beams of the beam array, and an adjacent area of the one first inspection area is not scanned with the beam array.

The sum of the one first inspection area and the adjacent area of the one first inspection area may be substantially the same as the area of the quadrangle. The scanning may be performed while the stage is moving.

The method may further comprises redirecting the beam array after finishing scanning the plurality of first inspection areas to scan a plurality of second inspection areas. The method may further comprises measuring a critical dimension of a pattern from an image obtained by the scanning of a first inspection area.

BRIEF DESCRIPTION OF THE DRAWINGS

Exemplary embodiments of the inventive concept will be more clearly understood from the following detailed description taken in conjunction with the accompanying drawings in which.

DETAILED DESCRIPTION

Figure 1:
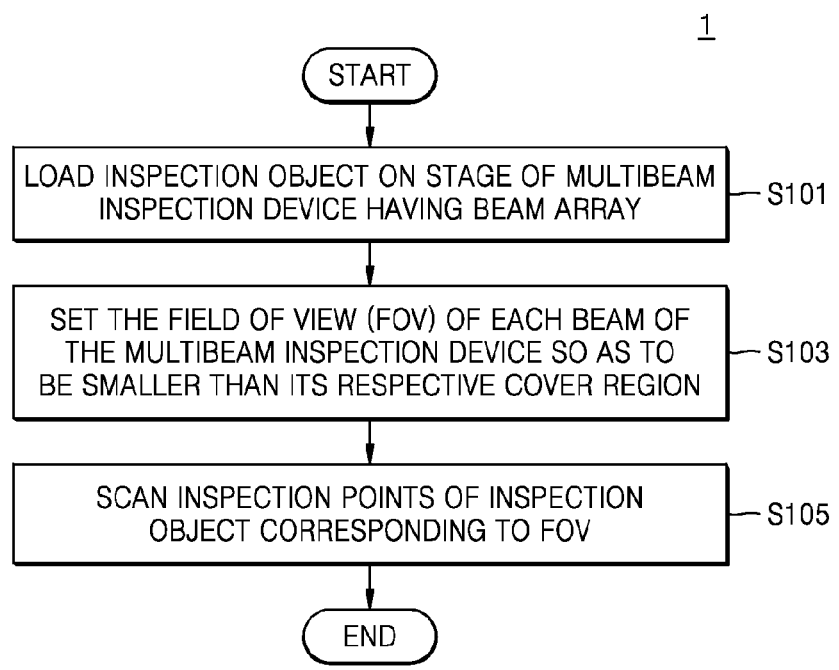
FIG. 1 is a flowchart of a method of inspecting a surface according to an exemplary embodiment.

The present disclosure will be described more fully hereinafter with reference to the accompanying drawings, in which exemplary embodiments of the inventive concept are shown. This inventive concept may, however, be embodied in many different forms and should not be construed as limited to the exemplary embodiments set forth herein. These example embodiments are just that—examples—and many implementations and variations are possible that do not require the details provided herein. It should also be emphasized that the disclosure provides details of alternative examples, but such listing of alternatives is not exhaustive. Furthermore, any consistency of detail between various examples should not be interpreted as requiring such detail—it is impracticable to list every possible variation for every feature described herein. The language of the claims should be referenced in determining the requirements of the invention. In the drawings, the sizes of layers and regions may be exaggerated for clarity. The same reference numerals are used to denote the same elements, and repeated descriptions thereof will be omitted.

It will be understood that, although the terms "first," "second," etc. may be used herein to describe various elements, components, regions, layers and/or sections, these elements, components, regions, layers and/or sections should not be limited by these terms, unless the context so indicates. Thus, a first element, component, region, layer or section discussed below could be termed a second element, component, region, layer or section without departing from the teachings of the inventive concept.

Unless otherwise defined, all terms (including technical and scientific terms) used herein have the same meaning as commonly understood by one of ordinary skill in the art to which this inventive concept belongs. It will be further understood that terms, such as those defined as commonly used dictionaries, should be interpreted as having a meaning that is consistent with their meaning in the context of the relevant art and this specification and will not be interpreted in an idealized or overly formal sense unless explicitly so defined herein.

When some embodiments may be embodied otherwise, respective process steps described herein may be performed otherwise. For example, two process steps described in a sequential order may be performed at substantially the same time or in reverse order.

Variations from the shapes of the illustrations as a result, for example, of manufacturing techniques and/or tolerances, are to be expected. Thus, the inventive concepts should not be construed as limited to the particular shapes of regions illustrated herein but are to include deviations in shapes that result, for example, from manufacturing.

In addition, sizes of components in the drawings may be exaggerated for convenience of explanation. For example, since sizes and thicknesses of components in the drawings are arbitrarily illustrated for convenience of explanation, the inventive concepts are not limited thereto.

It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

It will be understood that when an element is referred to as being "connected" or "coupled" to or "on" another element, it can be directly connected or coupled to or on the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.). However, the term "contact," as used herein refers to direct contact (i.e., touching) unless the context indicates otherwise.

Terms such as "same," "equal," "planar," or "coplanar," as used herein when referring to orientation, layout, location, shapes, sizes, amounts, or other measures do not necessarily mean an exactly identical orientation, layout, location, shape, size, amount, or other measure, but are intended to encompass nearly identical orientation, layout, location, shapes, sizes, amounts, or other measures within acceptable variations that may occur, for example, due to manufacturing processes. The term "substantially" may be used herein to reflect this meaning. Terms such as "exactly" or "identical" may be used to indicate no such variation.

As used herein, the term "and/or" includes any and all combinations of one or more of the associated listed items. Expressions such as "at least one of," when preceding a list of elements, modify the entire list of elements and do not modify the individual elements of the list.

FIG. 1 is a flowchart of a method 1 of inspecting a surface according to an exemplary embodiment.

Referring to FIG. 1, an inspection object is loaded on a stage of a multibeam inspection device configured to generate a beam array (S101). Then, each field of view (FOV) of beams of the beam array generated by the multibeam inspection device may be set to be smaller than a cover region (S103). Afterwards, a plurality of inspection points on the inspection object, the inspection points respectively corresponding to the FOVs, may be scanned with the beam array (S105). A detailed description in this regard will be described below with reference to FIGS. 2 to 5. A cover region C described herein may also be referred to as a coverage region. For example, a coverage region C may be a region of a square or a rectangle having a side that has the same length as a pitch between the beams of the beam array. For example, a coverage region C may correspond to a region that a beam of the beam array covers for an inspection. An "inspection point" as described herein refers to an inspection area. For example, inspection areas may correspond to respective field of views (FOVs) of beams of a beam array.

Figure 2:
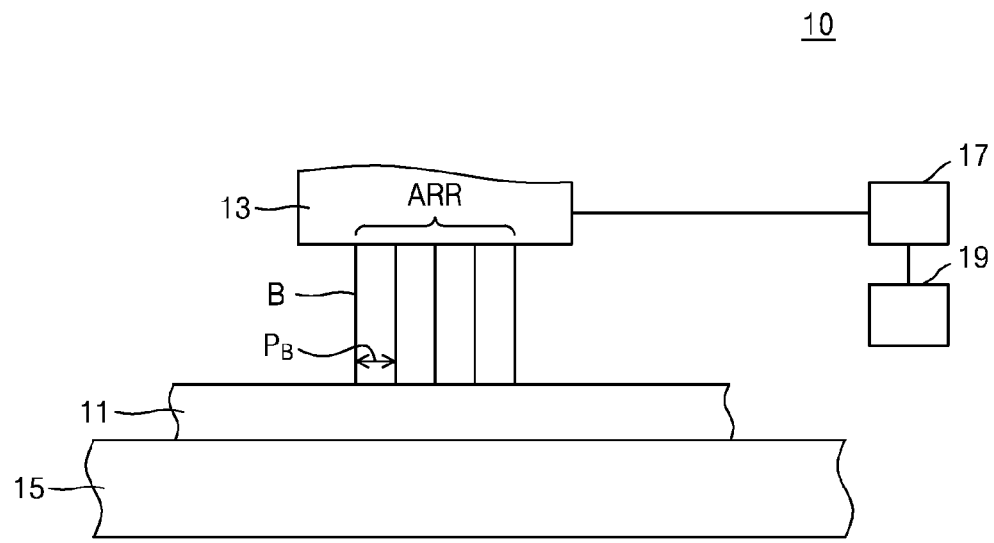
FIG. 2 is a schematic side view of a multibeam inspection device used in a method of inspecting a surface according to an exemplary embodiment.

FIG. 2 is a schematic side view of a multibeam inspection device 10 used in a method of inspecting a surface according to an exemplary embodiment.

Referring to FIGS. 1 and 2, the multibeam inspection device 10 may include a scanner 13, a stage 15, a controller 17, and a display unit 19.

The scanner 13 may include a source unit and a detector. The source unit may generate a beam array ARR and scan an inspection object 11 with the beam array ARR. The beam array ARR may include a plurality of beams B separated from each other by certain pitches $P_B$. The plurality of beams B may be deflected in a scanning direction by controlling voltage applied to the source unit. The detector may detect an intensity, a phase and/or a wavelength of the beams B reflected from the inspection object 11. The detector may include an imaging device configured to acquire images and generate a surface state image of the inspection object 11.

The inspection object 11 is loaded on the stage 15 (S101) to face the scanner 13 radiating the beams B. The stage moves 15 two-dimensionally in horizontal directions and changes scanning regions of the inspection object 11. The stage 15 is not limited to the horizontal movement and the stage 15 may also move vertically.

The controller 17 exchanges an electrical signal with the scanner 13. The controller 17 may obtain a surface state image corresponding to each position of the inspection object 11 by receiving data regarding a position or/and a moving distance of the stage 15 and data detected by the detector. Furthermore, the controller 17 may calculate a critical dimension (CD) of light shielding patterns according to a difference of light and shade or color in the obtained image. The controller 17 may include a storage device configured to store various data and images.

The display unit 19 may be connected to the controller 60 and display the various data and images.

Figure 3:
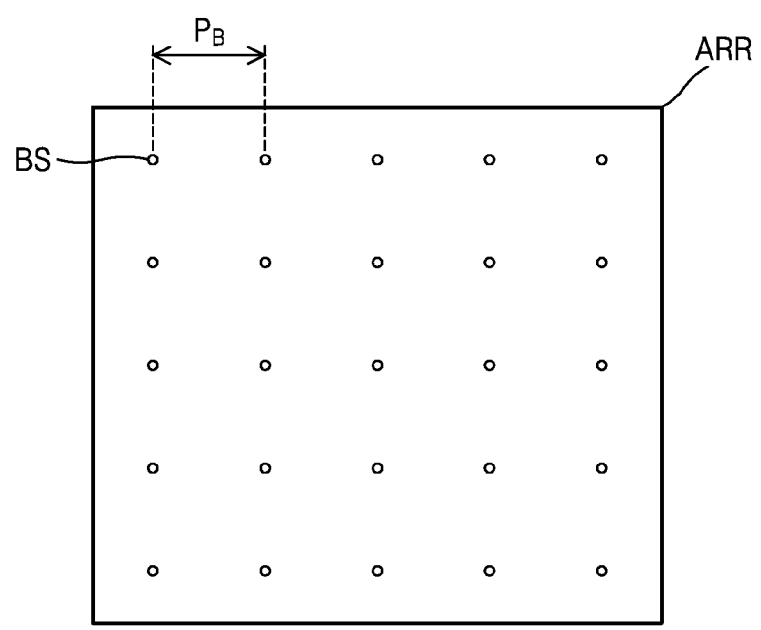
FIG. 3 is a plan view of a beam array, including a plurality of beams, generated by the multibeam inspection device of FIG. 2.

FIG. 3 is a plan view of the beam array ARR generated by the multibeam inspection device 10 of FIG. 2.

Referring to FIGS. 2 and 3, the scanner 13 of the multibeam inspection device 10 may generate the beam array ARR including the beams B. The beams B of FIG. 2 may be emitted by a beam source BS of FIG. 3. The beams B are arranged in a matrix shape of 5×5 and are separated from each other by certain pitches $P_B$. The beams B forming the beam array ARR scan inspection points of the inspection object 11 respectively and simultaneously according to positions thereof.

As the beams B are simultaneously supplied to scan the inspection object 11, partial regions of the inspection object 11 may be scanned more than once by the beams B. In order to avoid double scanning of the partial regions, each of the beams B may have a cover region defined by pitches $P_B$ between the beams B. For example, the cover region of each of the beams B is a specific scanning region that does not overlap a scanning region of another beam. This will be described in detail with reference to FIG. 4.

The beams B may generate the beam array ARR by being arranged in a matrix shape of 5×5 but the invention is not limited thereto. In some embodiments, the beams B may generate a beam array ARR by being arranged in a matrix shape of M×N (M≥1, N≥1, M*N≠1). In some embodiments, the beams B may be arranged not in a matrix shape but in other various arrangements.

Figure 4:
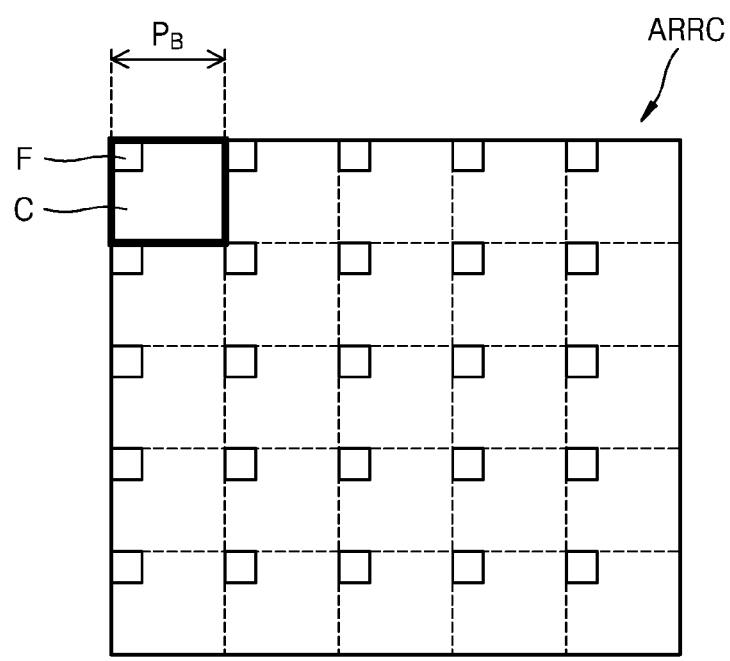
FIG. 4 is a view of the beams of FIG. 3 in a state where the beams are set to respectively have a field of view (FOV) smaller than a cover region of an inspection object, according to a method of inspecting a surface according to an exemplary embodiment.

FIG. 4 is a view of each cover region C and each field of view (FOV) F of each of the beams B forming the beam array ARR of FIG. 3, according to the method 1 of inspecting a surface according to an exemplary embodiment.

Referring to FIGS. 1, 3 and 4, each of the beams B of FIG. 3 may have the cover region C defined by pitches $P_B$ between the beams B. For example, each cover region C of the beams B is a specific scanning region that does not overlap a scanning region of another beam. Therefore, the entire cover region ARRC of the beam array ARR is formed by the sum of all cover regions C of the beams B.

According to certain embodiments, an inspection method using a multibeam inspection device, the FOV of each of the beams B may be equal to or larger than the cover regions C thereof. For example, in a method of inspecting a surface, an image of the entire cover region ARRC of the beam array ARR is obtained by scanning all of the cover regions C of the beams B. When this method is performed for the whole area of inspection points of the inspection object, it is possible to precisely inspect the entire surface of the inspection object, but it may take too much time to perform the inspection. When the inspection is performed only for a specific region of the inspection object in order to reduce the inspection time, it may be difficult to predict a uniformity of the whole area of the inspection object. The uniformity of the whole area of the inspection object may be related to a pattern, a defect rate, or a thickness thereof.

According to the method 1 of inspecting a surface according to an exemplary embodiment, the FOV F of each of the beams B generated by the multibeam inspection device 10 may be set to be smaller than the cover region C thereof (S103).

When the FOV F of each of the beams B is set to be smaller than the cover region C thereof, it may be difficult to obtain the entire image corresponding to the entire cover region ARRC of the beam array ARR. However, it may be beneficial to obtain at high speed images of inspection points located in the entire cover region ARRC with fixed intervals. Therefore, it may greatly reduce a scanning time while more accurately predicting at a relatively high speed the uniformity of the whole area of the inspection object by scanning and obtaining the images of the inspection points located throughout the inspection object with fixed intervals. The uniformity of the whole area of the inspection object may be related to a pattern, a defect rate, or a thickness thereof.

For example, in certain embodiments, the scanning time of an inspection object by using a multibeam inspection device is proportional to the scanning area and is inversely proportional to the cross sectional areas of the beams B and to the number of the beams B. When a lateral side and a longitudinal side of the FOV F of each of the beams B are respectively set to be $1/10$ times of sides of the cover region C thereof, the scanning area may be reduced to be $1/100$ times compared to the case when the FOV F of each of the beams B is equal to the cover region C thereof. Accordingly, the scanning time may be reduced to be $1/100$ times. For example, according to the method 1 of inspecting a surface according to an exemplary embodiment, the inspection time may be reduced to be in a range of several hours to several tens of hours from the inspection time that takes several tens to several hundred of days depending on the areas of the inspection objects while more accurately predicting the uniformity of the whole area of the inspection object.

The FOV F of each of the beams B may be freely set by considering a throughput of the inspection device to be in a range smaller than the cover region C.

Figure 5:
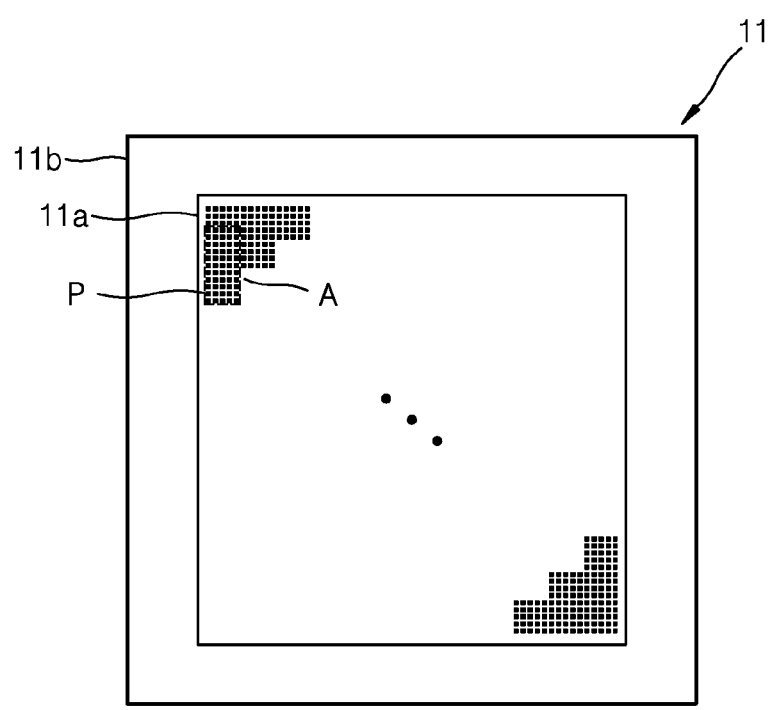
FIG. 5 is a view of a plurality of inspection points inspected according to a method of inspecting a surface according to an exemplary embodiment.

FIG. 5 is a view of inspection points P of an inspection object scanned according to the method 1 of inspecting a surface according to an exemplary embodiment.

Referring to FIGS. 1, 4 and 5, the inspection object 11 may include an inspection region 11a and a peripheral region 11b. The beam array ARR of FIG. 3 may scan inspection points P corresponding to each of the FOVs F throughout the inspection region 11a (S105). Only a part of the scanned inspection points P is illustrated in FIG. 5, however, the inspection points P may be distributed throughout the inspection region 11a with fixed intervals.

In some embodiments, the inspection object 11 may be, for example, a photomask. For example, light shielding patterns may be formed in the inspection region 11a. Accordingly, when the method 1 of inspecting a surface is used to inspect a photomask, the method 1 may further include an operation of measuring a CD of light shielding patterns based on images obtained from the inspection points of the photomask. In this case, it is possible to inspect critical dimension uniformity (CDU) of the light shielding patterns of interest at the inspection points of the photomask.

The photomask described above may be used to selectively expose a photosensitive film formed on a wafer in a photolithography process of a semiconductor device. Accordingly, the photomask may be formed by arranging a light shielding pattern or a light shielding material on a surface of a transparent substrate. As the light shielding patterns define semiconductor patterns formed on a wafer, the CD such as line widths of the light shielding patterns and/or intervals between the light shielding patterns is a very important factor in manufacturing a semiconductor device.

In the case of a photomask used in manufacturing a logic element, patterns of interest may be irregularly scattered as non-repetitive patterns over the photomask. Accordingly, it is beneficial to inspect CDs of the patterns throughout the photomask. However, in the case of scanning the whole area of the photomask, it may take too much time even if a multibeam inspection device is used.

According to the method 1 of inspecting a surface according to an exemplary embodiment, it is possible to reduce the FOV of each of the beams generated by a multibeam inspection device and scan the whole area of a photomask with fixed intervals.

For example, CDU of a photomask may be predicted by inspecting points located uniformly over the whole area of the photomask without inspecting the whole area of the photomask. For example, images are collectively obtained from inspection points located throughout the photomask with fixed intervals, and many CDs may be obtained from images from which patterns of interest are picked up from among the collectively obtained images. The CDs are calculated at the inspection points throughout the photomask, and thus, the CDU of the photomask may be more accurately predicted while greatly reducing the scanning time.

Scanning the whole area to be inspected in the inspection region 11a may be performed by moving a stage that supports the inspection object 11. In some embodiments, scanning of an inspection point P may be simultaneously performed while the stage is moving so that a following inspection point P may be quickly scanned. Therefore, each beam may be deflected while the stage is moving in order to finish scanning the inspection point P. If the stage is moving toward another inspection point while simultaneously scanning any one of the inspection points, the inspection time may be reduced as the stage moving time is included in the total inspection time.

Furthermore, each of the inspection points P may be scanned several times while the stage is moving. In some embodiments, each of the inspection points P may be scanned a plurality of times with an identical beam. In other embodiments, each of the inspection points P may be scanned a plurality of times with different beams.

An "A" portion in the inspection region 11a is used to describe a scanning process of the inspection points P according to stage movement, and this will be described in detail with reference to FIGS. 8 to 12.

Figure 6:
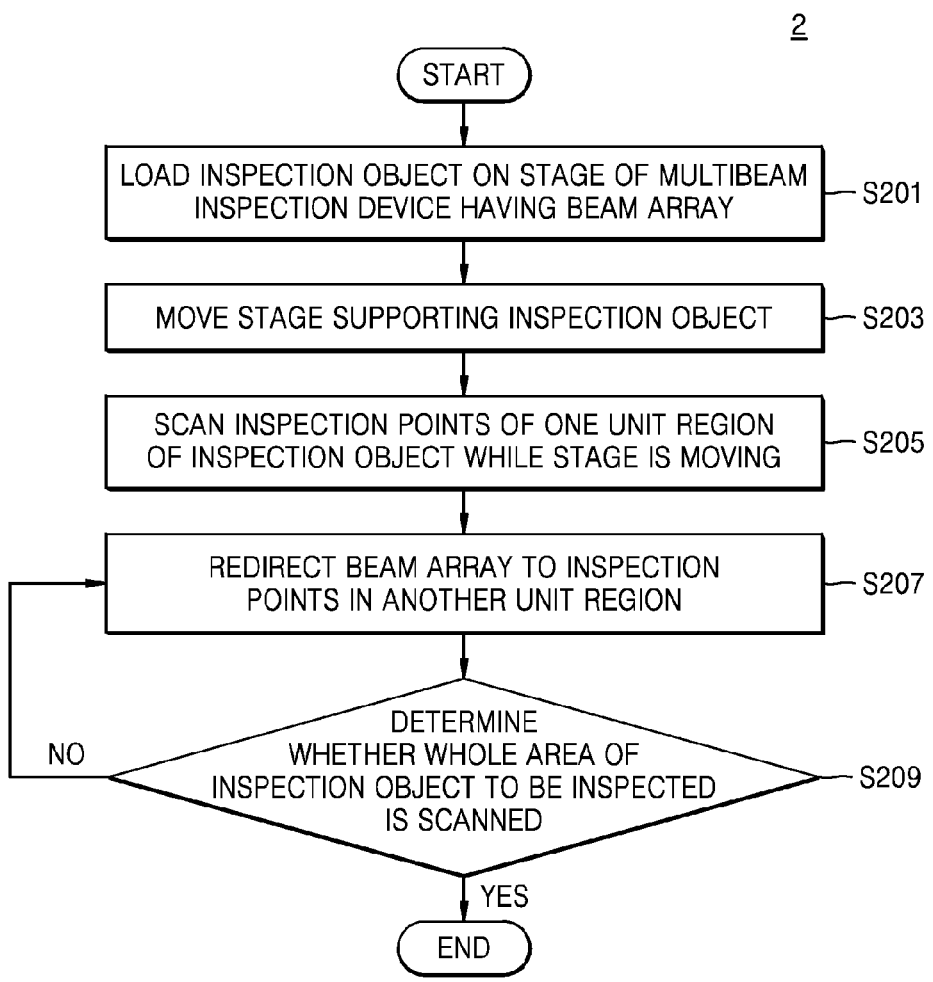
FIG. 6 is a flowchart of a method of inspecting a surface according to another exemplary embodiment.

FIG. 6 is a flowchart of a method 2 of inspecting a surface according to another exemplary embodiment.

Referring to FIG. 6, an inspection object is loaded on a stage of a multibeam inspection device configured to generate a beam array (S201). Next, the stage that supports the inspection object is moved (S203). Afterwards, the beam array scans inspection points in any one of unit regions of the inspection object while the stage is moving (S205). After finishing scanning of the inspection points in any one of the unit regions, the beam array is deflected from the inspection points in any one of the unit regions to inspection points in another unit region (S207). After determining whether the whole area of the inspection object to be inspected has been scanned (S209), the scanning (S205) and the beam array deflection (S207) may be performed repeatedly. This will be described in detail with reference to FIGS. 7A to 7D.

FIGS. 7A to 7D are side views of an inspection object 11 undergoing a scanning process while a stage 15 is moving according to the method 2 of inspecting a surface according to an exemplary embodiment.

Referring to FIGS. 7A to 7D, a scanner 13 generates a beam array ARR including a plurality of beams B1 to B5. The inspection object 11 loaded on the stage 15 has a plurality of unit regions corresponding to the beam array ARR. A scanning time corresponding to any one of the unit regions may be, for example, 3 ms, but the present invention is not limited thereto. The scanning time of the unit region may be changed arbitrarily according to the range of an FOV, the performance of an inspection device, or inspection conditions.

The stage 15 moves in an arrow direction 15d while a first unit region U1 is being scanned. For example, it may reduce the total inspection time for the stage to move because the stage moving and the inspection are performed simultaneously, and a second unit region U2 may be immediately scanned after scanning the first unit region U1. Accordingly, after finishing the scanning corresponding to the first unit region U1, the scanning corresponding to the second unit region U2 may be performed immediately.

The beams B1 to B5 may be deflected so as to scan along the moving first unit region U1. Immediately after the scanning of the first unit region U1, the beams B1 to B5 may be deflected so as to scan the second unit region U2. The deflection of the beams B1 to B5 may be realized through a voltage control function included in the inspection device. For example, the direction of the beams B1 to B5 may change during the scanning of the first unit region U1, and immediately before the scanning of the second unit region U2, the direction of the beams B1 to B5 may be adjusted to a direction to properly start scanning the second unit region U2. This redirection process may also be performed in the following processes when the scanning transfers one unit region to another unit region. The deflection of a beam array described herein may be more generally referred to as redirection of a beam array.

Figure 7A:
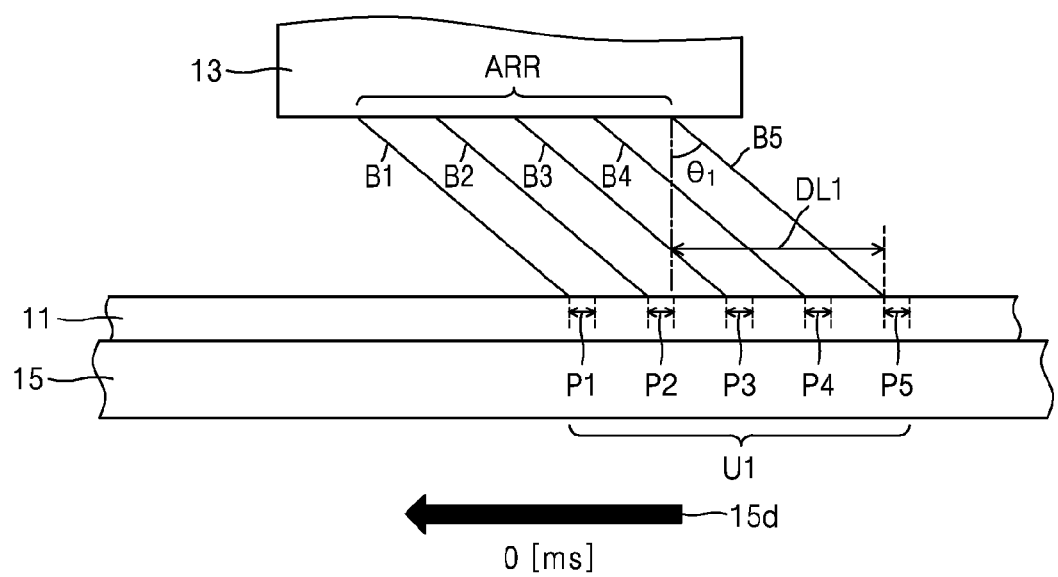
FIGS. 7A to 7D are side views of an inspecting object inspected via the method of inspecting a surface of FIG. 6.
Figure 7B:
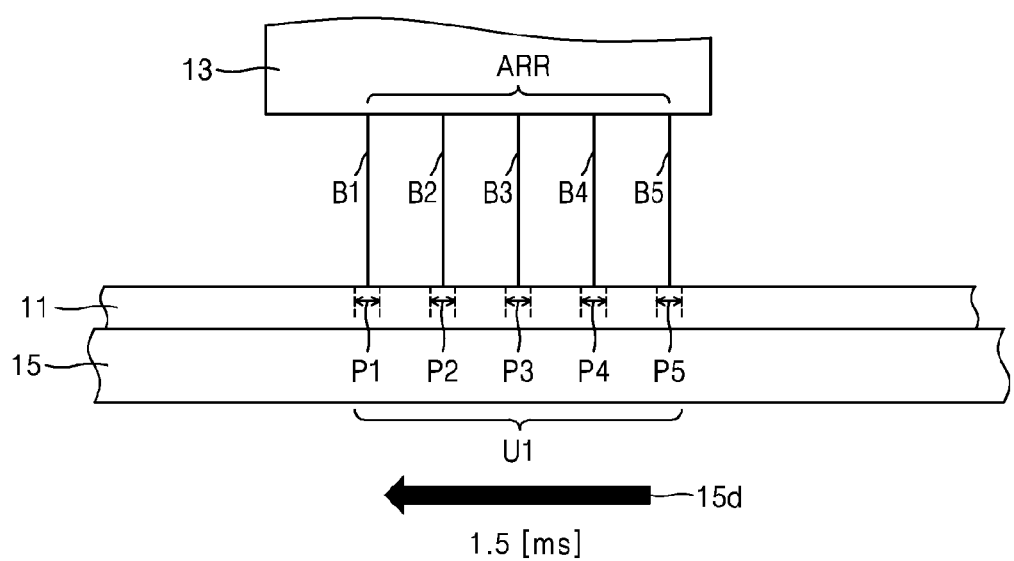
Figure 7C:
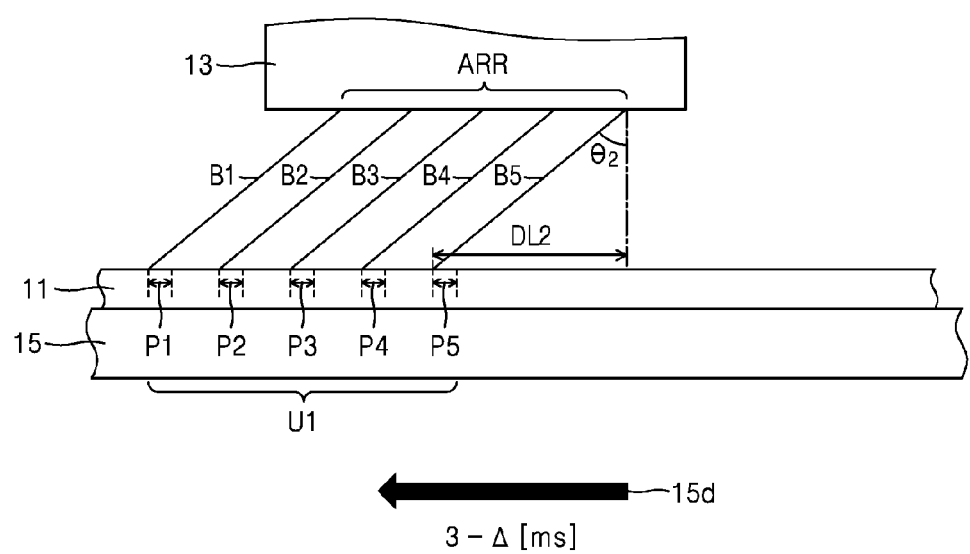

For example, referring to FIGS. 7A to 7C, the beams B1 to B5 scan inspection points P1 to P5 of the first unit region U1 during a time range from 0 ms to 3−Δ ms. Δms represents a fine time range and 3−Δms may mean a time just before time 3 ms or a little less than 3 ms (e.g., within 0.1% of 3 ms). As described above with respect to FIG. 4, the inspection points P1 to P5 may be adjusted so as to be smaller than each cover region C of the beams B1 to B5. In this case, the beams B1 to B5 perform scanning along the moving inspection points P1 to P5 while being deflected by a first angle θ1 to a second angle θ2, for example, by a first deflection distance DL1 to a second deflection distance DL2. For example, the beams B1 to B5 may change from θ1 to θ2 during the scanning of the inspection points P1 to P5.

Figure 7D:
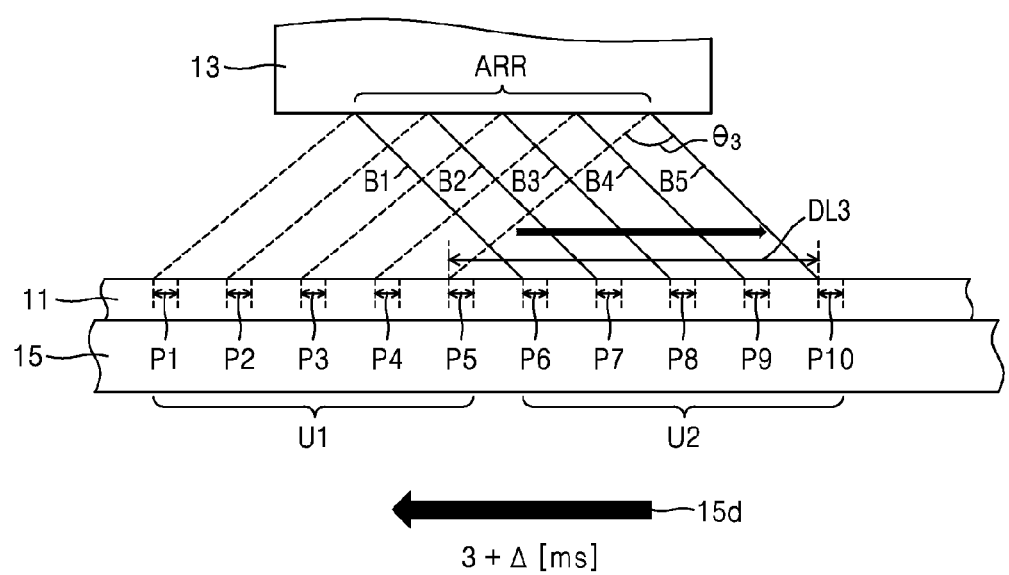

Referring to FIGS. 7C and 7D, the scanning corresponding to the inspection points P1 to P5 of the first unit region U1 is finished at time 3−Δms, which is close to time 3 ms, and the beams B1 to B5 may be respectively deflected to inspection points P6 to P10 of the second unit region U2 by a third angle θ3, for example, a third deflection distance DL3 at time 3 ms. Therefore, scanning corresponding to the inspection points P6 to P10 of the second unit region U2 may immediately start from time 3+Δms just after time 3 ms.

The second unit region U2 may be a region which does not overlap the first unit region U1. For example, the third deflection distance DL3 may be equal to the length of a unit region in the stage moving direction 15d. The third deflection distance DL3 may be substantially equal to the sum of pitches between the beams B1 to B5 arranged in the stage moving direction 15d. The inspection points P1 to P5 in the first unit region U1 and the inspection points P6 to P10 in the second unit region U2 may be scanned once, respectively.

FIGS. 7A to 7D illustrate the inspection points being scanned once as the unit regions do not overlap each other, but the present exemplary embodiment is not limited thereto. A plurality of scans may be performed on the inspection points while the stage is moving. In some embodiments, a plurality of scans may be performed on the inspection points with different beams, respectively. This will be described below with reference to FIGS. 8 to 10G. In some embodiments, a plurality of scans may be performed on the inspection points with an identical beam. This will be described below with reference to FIGS. 11 to 12F.

Following scanning of the second unit region U2 may be the same as those described with respect to FIGS. 7A to 7D. By this inspection method, a plurality of unit regions may be inspected, and therefore, the whole surface to be inspected in the inspection object 11 may be inspected.

FIGS. 7A to 7D illustrate a case of when the speed of the stage and the scanning speed of the unit region are the same, but the present invention is not limited thereto. In some embodiments, the speed of the stage may be faster than the scanning speed of the unit region. In this case, movement of the stage may be temporarily interrupted until the scanning corresponding to the unit region is finished. Afterwards, the movement of the stage may be restarted immediately after finishing the scanning of the unit region.

In some embodiments, the speed of the stage may be slower than the scanning speed of the unit region. In this case, scanning idle time may be generated while the stage moves until a following unit region moves to a scanning position after the scanning of the unit region is finished. In this case, the inspection conditions may be adjusted by extending the FOV of each of the beams B1 to B5 forming the beam array ARR and expanding the inspection points P1 to P10.

In general, when inspection points of an inspection object is distributed discontinuously, the stage moves so that another inspection point may be scanned after finishing scanning any one of the inspection points. In this case, inspection time may extend due to not only scanning time itself generation but also stage moving time delay.

According to the surface inspection method 2 of an exemplary embodiment, stage movement toward another inspection point may be simultaneously performed while scanning any one of the inspection points. Therefore, it is possible to reduce the total inspection time as the stage moving time is included in the total inspection time.

Figure 8:
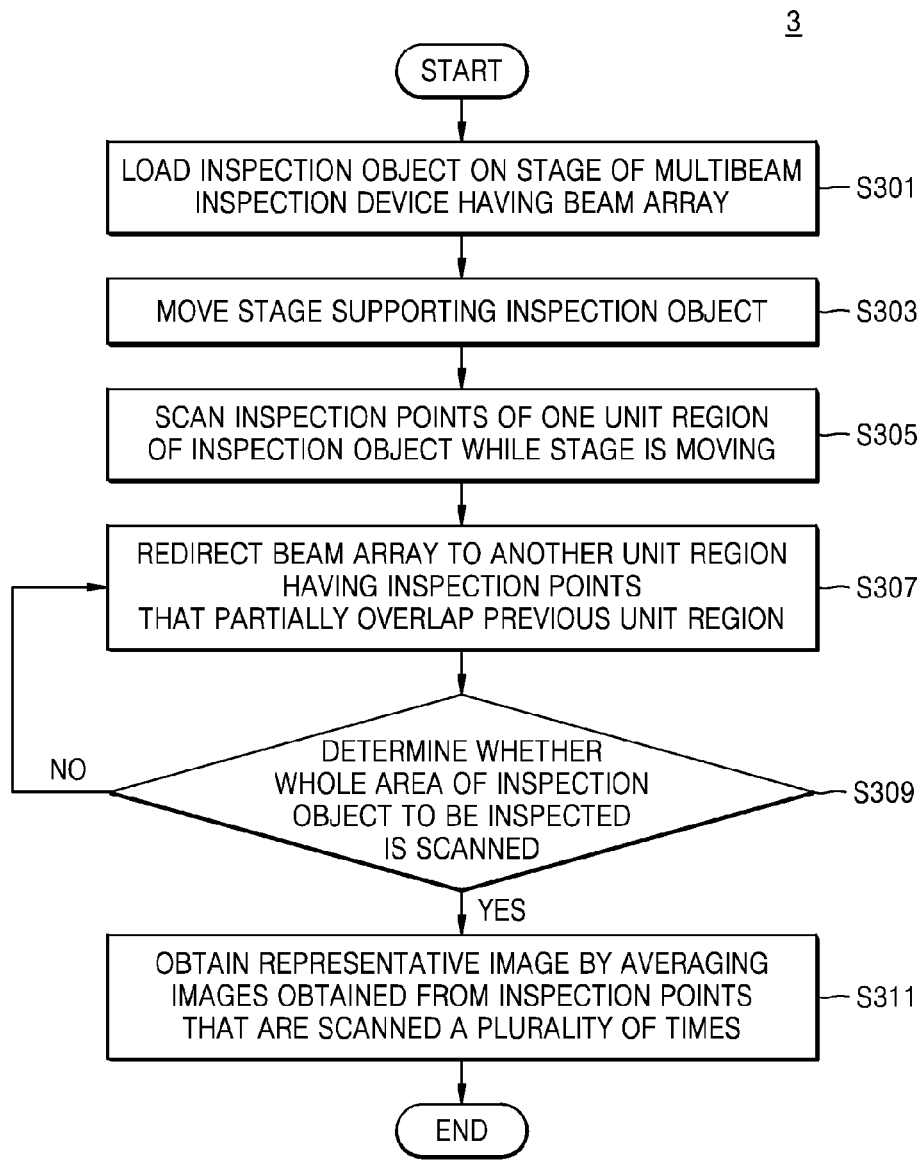
FIG. 8 is a flowchart of a method of inspecting a surface according to another exemplary embodiment.

FIG. 8 is a flowchart of a method 3 of inspecting a surface according to another exemplary embodiment. The method 3 of inspecting a surface of FIG. 8 is similar to the surface inspection method 2 of FIGS. 6 to 7D, however, it is different from the surface inspection method 2 in partial overlapping of a plurality of unit regions. For example, a plurality of images may be obtained by plural times of scanning of each inspection point. The images corresponding to an identical inspection point may be used for obtaining a representative image having high reliability through image averaging.

Referring to FIG. 8, first, an inspection object is loaded on a stage of a multibeam inspection device configured to generate a beam array (S301). A stage that supports the inspection object moves (S303). Next, the beam array scans inspection points in any one unit region of the inspection object while the stage is moving (S305). After finishing scanning of the inspection points in the unit region, the beam array is deflected to another unit region having inspection points that partially overlap the one unit region (S307). For example, the beam array may be deflected to other inspection points located at positions separated or shifted from the inspection points of the one unit region by a pitch $P_B$ of the beams. For example, the beam array may be redirected to another unit region located at a position shifted by a pitch $P_B$ of the beams from the one unit region. Accordingly, a plurality of images may be obtained by plural times of the scanning of the overlapping inspection points. After determining whether the whole area of the inspection object to be inspected has been scanned (S309), and when the whole area of the inspection object to be inspected has not yet been scanned, the scanning (S305) and the beam array deflection (S307) may be performed repeatedly. A representative image may be obtained by averaging the images obtained by scanning the inspection points a plurality of times (S311). This will be described in detail with reference to FIGS. 9A to 10G.

FIGS. 9A to 9E are side views of an inspection stage with an inspection object. The inspection points of the inspection object are scanned plural times with different beams respectively while the stage is moving, according to the method 3 of inspecting a surface according to an exemplary embodiment.

Referring to FIGS. 9A to 9E, the stage 15 moves in the arrow direction 15$d$ while a first unit region N1 from among a plurality of unit regions is being scanned. For example, the stage moving time may not increase of the total inspection time because the stage 15 moves during the inspection time of the first unit region N1 so that a second unit region N2 may be immediately scanned after scanning the first unit region N1. For example, the stage 15 moves simultaneously with the scanning of the first unit region N1. Accordingly, after finishing the scanning corresponding to the first unit region N1, the scanning corresponding to the second unit region N2 may be performed immediately.

The first unit region N1 may partially overlap the second unit region N2. For example, the first unit region N1 may include first to fifth inspection points P1 to P5 and the second unit region N2 may include second to sixth inspection points P2 to P6. For example, the second to fifth inspection points P2 to P5 may be scanned twice when the scanning of the second unit region N2 is performed after the scanning of the first unit region N1.

Figure 9A:
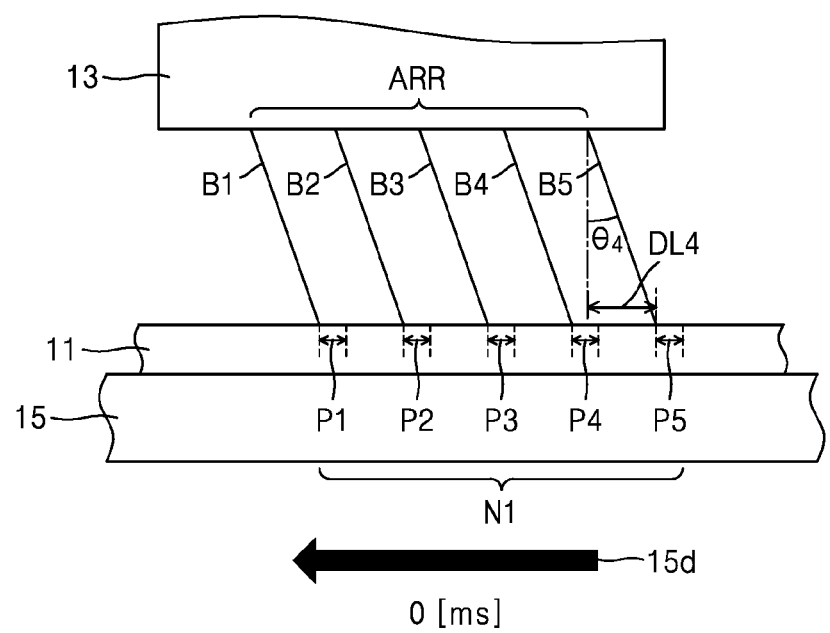
FIGS. 9A to 9E are side views of an inspecting object inspected via the method of inspecting a surface of FIG. 8.
Figure 9B:
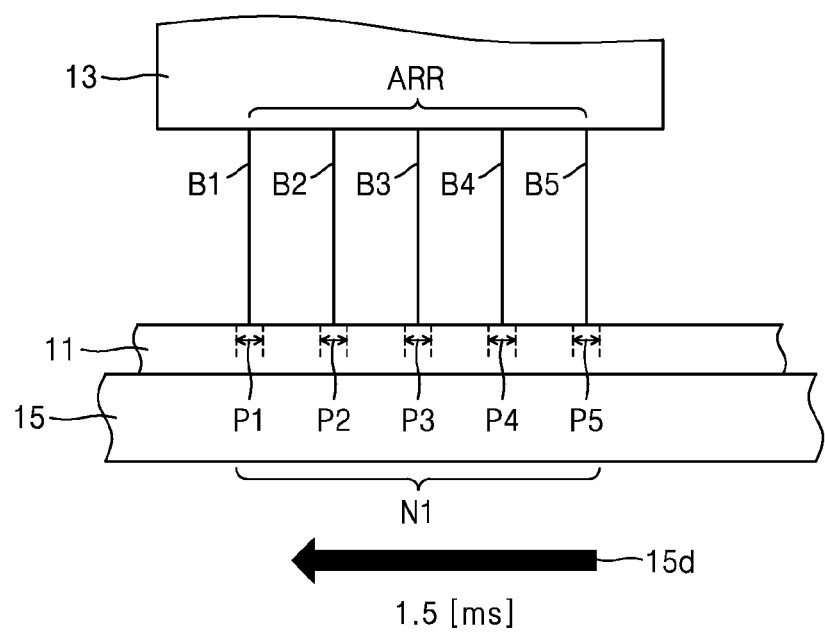
Figure 9C:
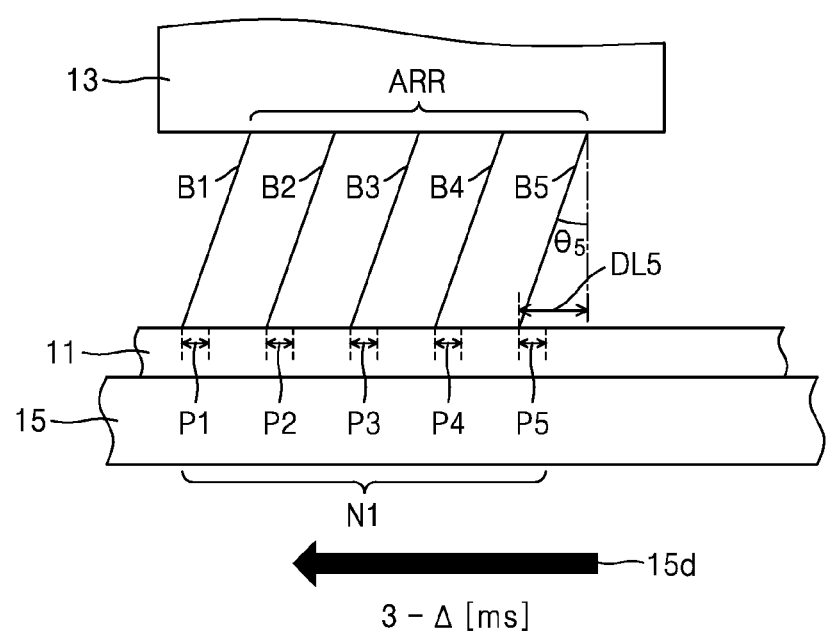

For example, referring to FIGS. 9A to 9C, the beams B1 to B5 scan the inspection points P1 to P5 of the first unit region N1 during a time range from 0 ms to 3−Δ ms. In this case, the beams B1 to B5 perform scanning along the moving inspection points P1 to P5 while being deflected by a fourth angle θ4 to a fifth angle θ5, for example, by a fourth deflection distance DL4 to a fifth deflection distance DL5.

Figure 9D:
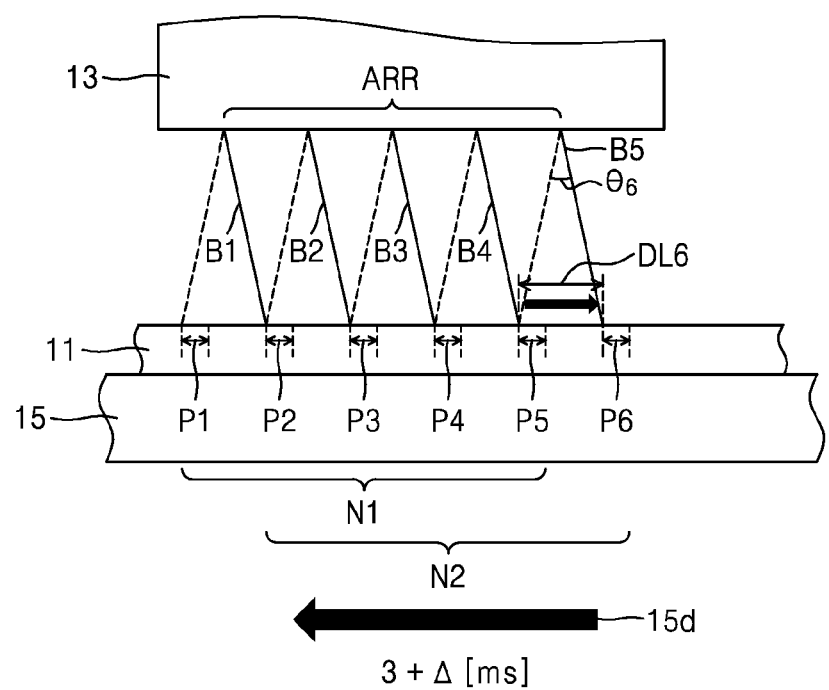

Referring to FIGS. 9C and 9D, the scanning corresponding to the inspection points P1 to P5 of the first unit region N1 is finished at time 3−Δ ms, which is close to time 3 ms, and the beams B1 to B5 may be respectively deflected to the inspection points P2 to P6 of the second unit region N2 by a sixth angle θ6, for example, a sixth deflection distance DL6 at time 3 ms. Therefore, scanning corresponding to the inspection points P2 to P6 of the second unit region N2 may immediately start from time 3+Δ ms just after time 3 ms.

The second unit region N2 may be a region which partially overlap the first unit region N1. For example, the sixth deflection distance DL6 may be substantially equal to the pitches between the beams B1 to B5 arranged in the same direction as the stage moving direction 15$d$. In this example, the second to fifth inspection points P2 to P5 are scanned twice by scanning the first and second unit regions N1 and N2 respectively.

Figure 9E:
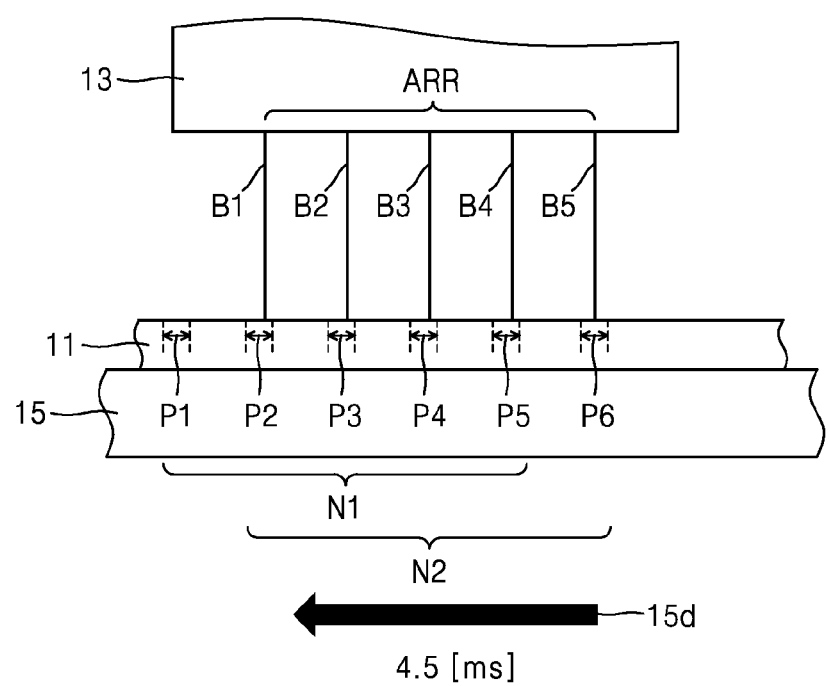

Referring to FIGS. 9D and 9E, the beams B1 to B5 scan the inspection points P2 to P6 of the second unit region N2 respectively after time 3+Δ ms. A following scanning of the second unit region N2 may be the same as or similar to those described with respect to FIGS. 9A to 9D. Accordingly, excluding a part of the inspection points of initial scanning, the inspection points may be scanned five times by the beams B1 to B5 respectively if the inspection points are included in five different unit regions respectively. A plurality of images obtained by scanning each of the inspection points a plurality of times may be used to obtain respective representative images through image averaging.

FIGS. 10A to 10G are plan views showing scanning an inspection object a plurality of times while the stage is moving, according to the method 3 of inspecting a surface of FIGS. 9A to 9E. FIGS. 10A to 10G correspond to portion A of FIG. 5 and illustratively show an inspection time of 0 to 18 ms. Shades of the inspection points become darker as the number of scans of the inspection points increases, however, this is only for convenience of explanation and the inspection points are not physically affected by the number of scans.

Referring to FIGS. 10A to 10G, the inspection object 11 has a plurality of unit regions corresponding to the beam array ARR as described above. The inspection points P1 to P10 may correspond to the FOV F that is smaller than the cover region C of the beams as described above with respect to FIG. 4. A plurality of beams (not shown) forming the beam array ARR are arranged in a matrix shape of 5×5 as described in FIG. 3.

Figure 10A:
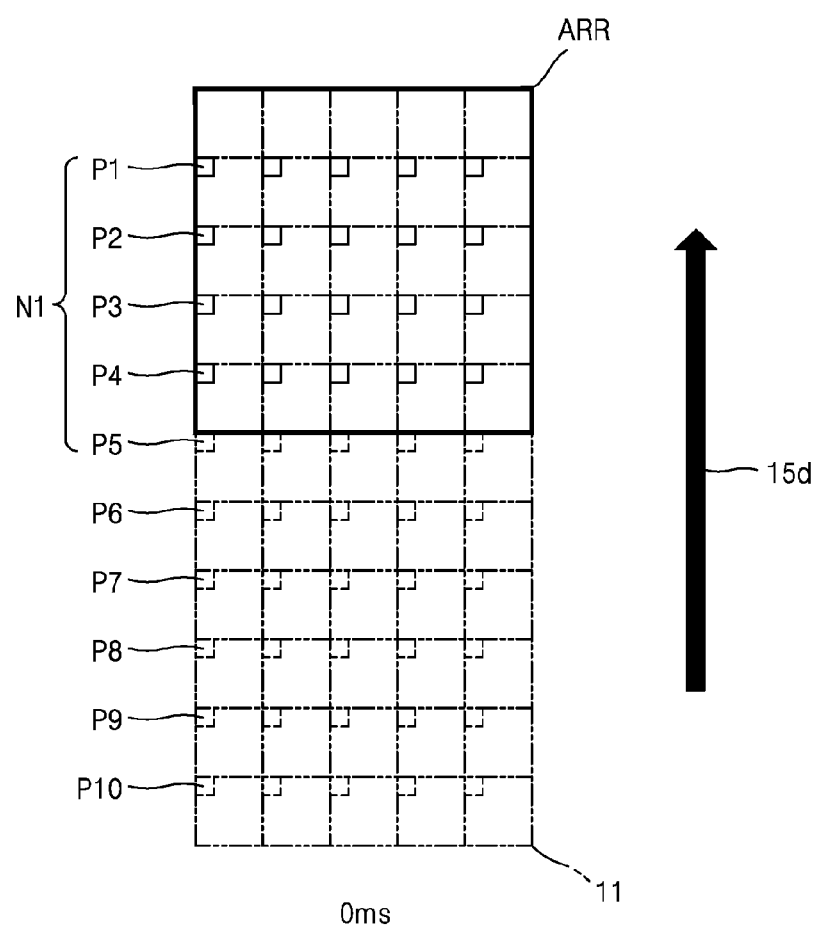
FIGS. 10A to 10G are plan views of an inspecting object inspected via the method of inspecting a surface of FIG. 8.
Figure 10B:
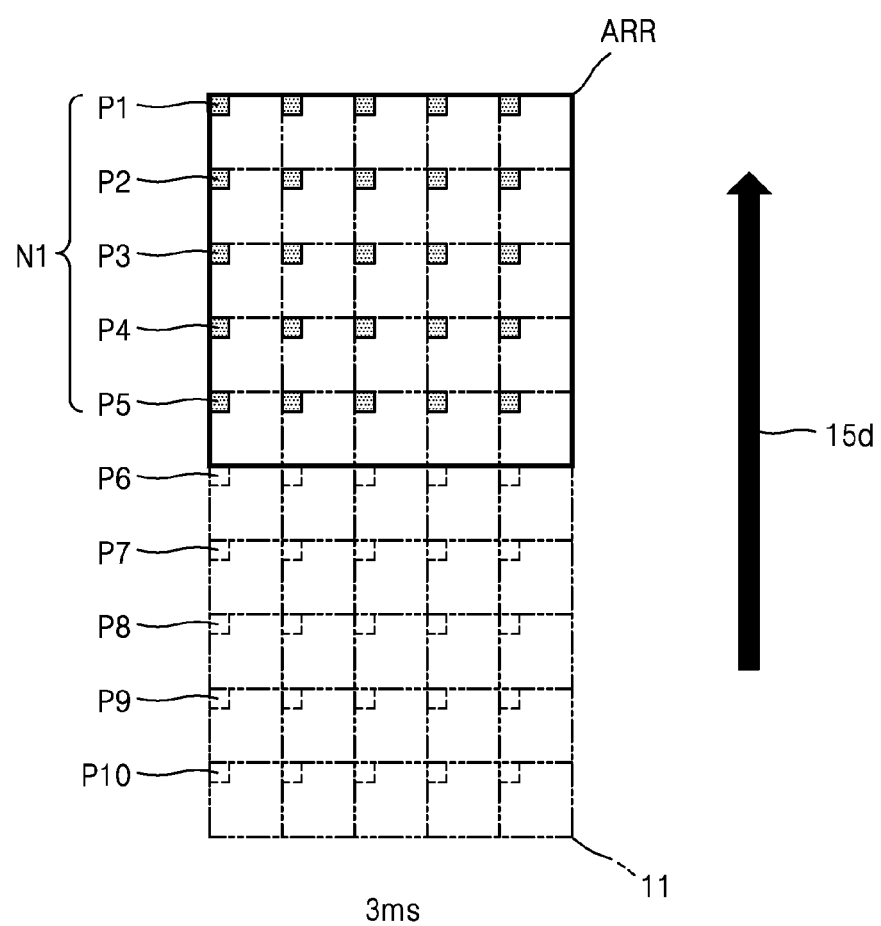

Referring to FIGS. 10A to 10B, the beam array ARR starts scanning first to fifth inspection points P1 to P5 of a first unit region N1 at time 0 ms and finishes one-time scanning of the first to fifth inspection points P1 to P5 of the first unit region N1 at time 3 ms. In order to start scanning of a second unit region N2 immediately after finishing the scanning of the first unit region N1, the stage moves from time 0 ms to time 3 ms while the scanning of the first unit region N1 is being performed. The beams may be deflected according to a stage moving speed in order to perform and finish scanning of the inspection points P1 to P5 of the first unit region N1 while the stage is moving.

Figure 10C:
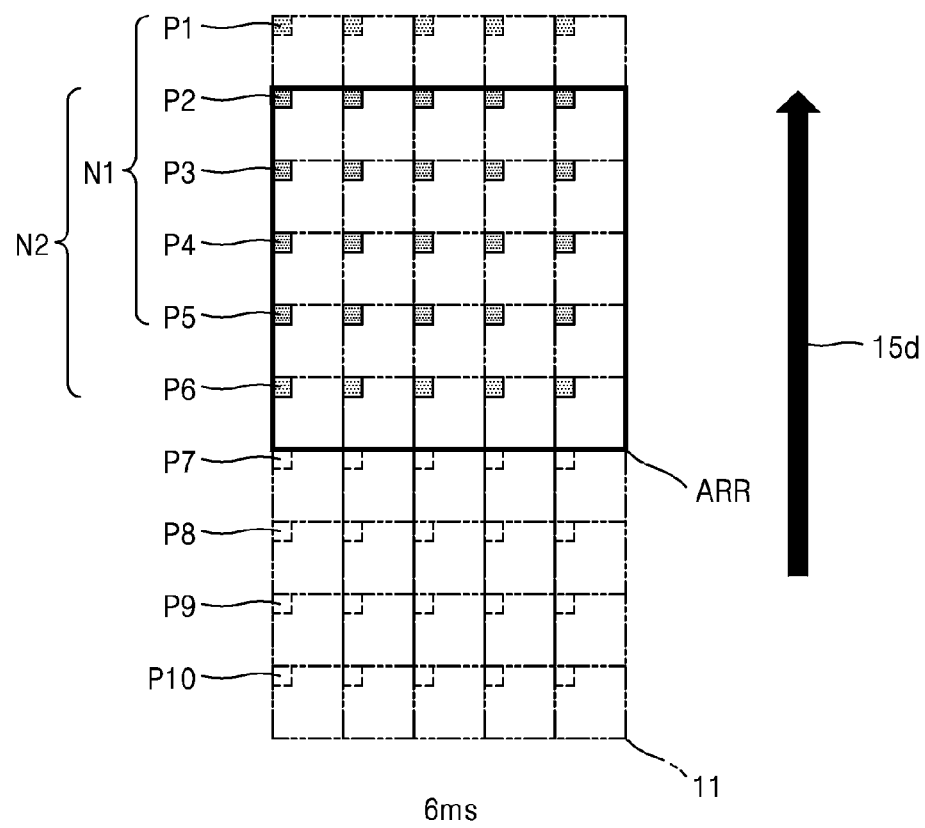

Referring to FIGS. 10B and 10C, the beam array ARR is deflected by a pitch between the beams and scans the second to sixth inspection points P2 to P6 of the second unit region N2 immediately after finishing scanning of the first to fifth inspection points P1 to P5 of the first unit region N1 at time 3 ms. For example, the scanning of the first unit region N1 may be finished immediately before time 3 ms and the scanning of the second unit region N2 may start immediately after time 3 ms so that the beams may be redirected after finishing scanning the first unit region N1 and before starting scanning the second unit region N2. This example may also be similarly applied to other transit periods described herein, for example, between the second to sixth unit regions N2, N3, N4, N5 and N6. The beam array ARR scans the second to sixth inspection points P2 to P6 of the second unit region N2 from time 3 ms to time 6 ms. In this case, the second to fifth inspection points P2 to P5 are scanned for the second time subsequently to the scanning of the first unit region N1. Following processes may take place similarly or identically.

Figure 10D:
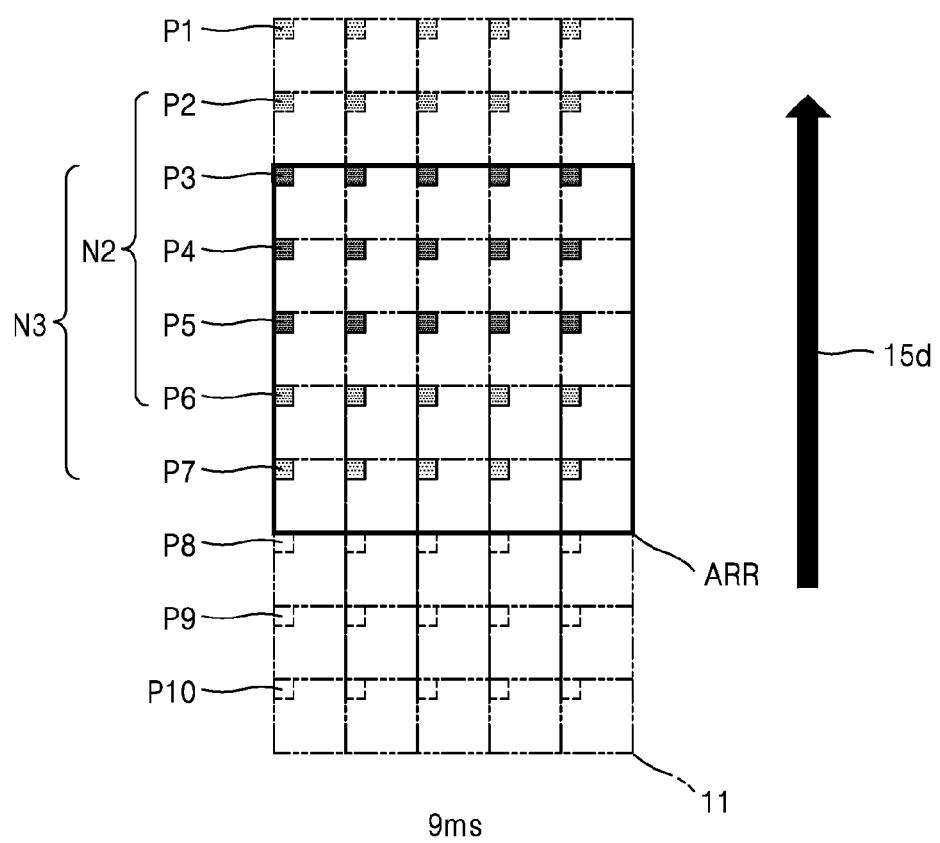

Referring to FIGS. 10C and 10D, the beam array ARR is deflected by a pitch between the beams and scans the third to seventh inspection points P3 to P7 of the third unit region N3 immediately after finishing scanning the second to sixth inspection points P2 to P6 of the second unit region N2 at time 6 ms. In this case, the third to fifth inspection points P3 to P5 are scanned for the third time subsequently to the scanning of the first and the second unit regions N1 and N2. The sixth inspection point P6 is scanned for the second time subsequently to the scanning of the second unit region N2.

Figure 10E:
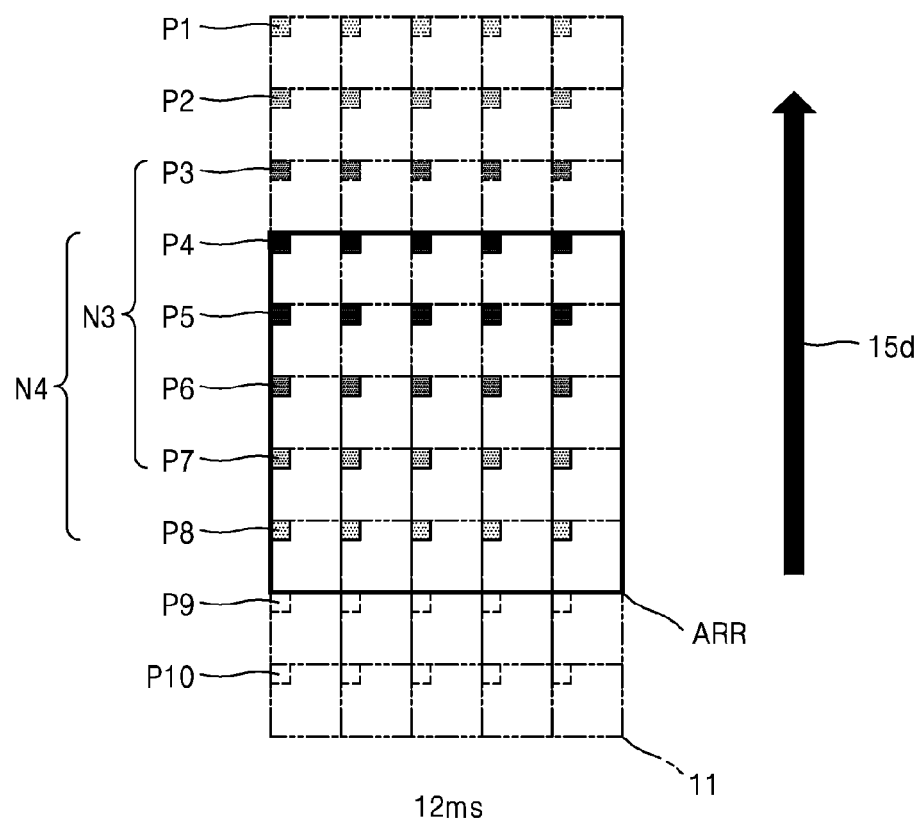

Referring to FIGS. 10D and 10E, the beam array ARR scans the fourth to eighth inspection points P4 to P8 of the fourth unit region N4 immediately after finishing scanning the third to seventh inspection points P3 to P7 of the third unit region N3 at time 9 ms. In this case, the fourth to fifth inspection points P4 and P5 are scanned for the fourth time. The sixth inspection point P6 is scanned for the third time and the seventh inspection point P7 is scanned for the second time.

Figure 10F:
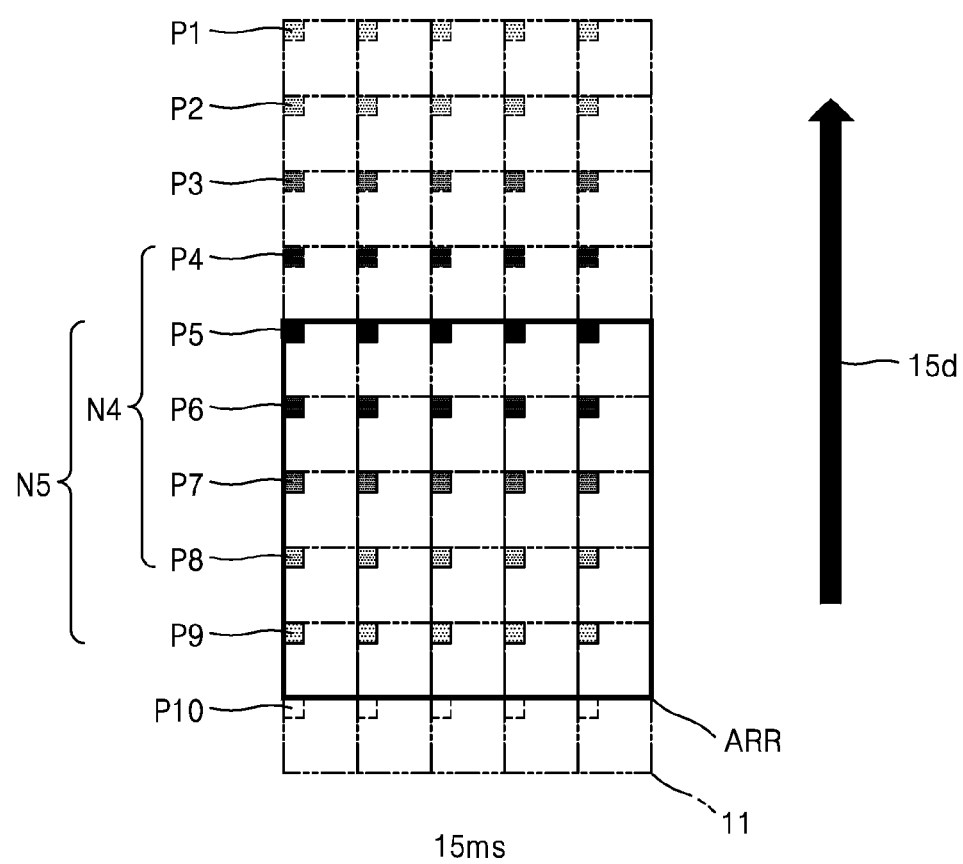

Referring to FIGS. 10E and 10F, the beam array ARR scans the fifth to ninth inspection points P5 to P9 of the fifth unit region N5 from time 12 ms to time 15 ms. In this case, the fifth inspection point P5 is scanned for the fifth time. The sixth inspection point P6 is scanned for the fourth time, the seventh inspection point P7 is scanned for the third time, and the eighth inspection point P8 is scanned for the second time.

Figure 10G:
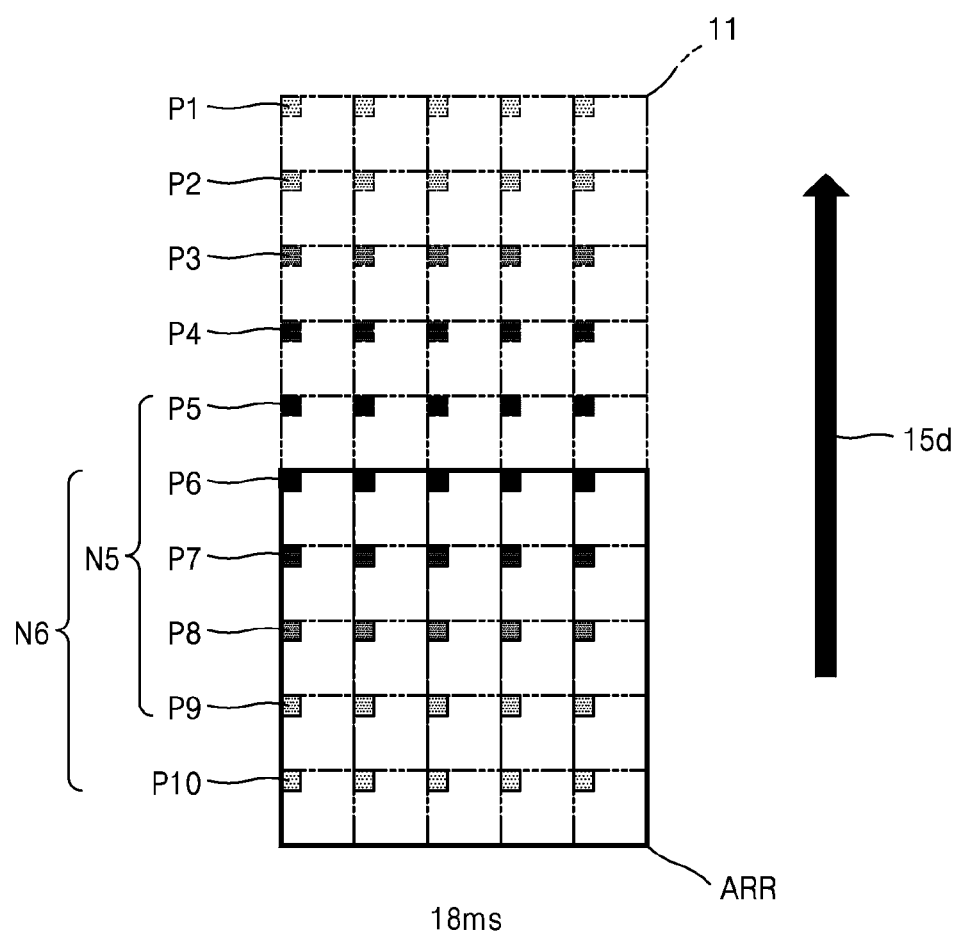

Referring to FIGS. 10F and 10G, the beam array ARR scans the sixth to tenth inspection points P6 to P10 of the sixth unit region N6 at time 15 ms to time 18 ms. In this case, the sixth inspection point P6 is scanned for the fifth time, the seventh inspection point P7 is scanned for the fourth time, the eighth inspection point P8 is scanned for the third time, and the ninth inspection point P9 is scanned for the second time.

A following scanning may also be performed in the same or a similar manner as described above with respect to FIGS. 10A to 10G. Furthermore, each following inspection point may be scanned with a number of the beams, for the fifth time, excluding the first to fourth inspection points P1 to P4 of the initial inspection. A plurality of images obtained by scanning each of the inspection points a plurality of times may be used for obtaining a representative image of each inspection point through image averaging.

According to the method 3 of inspecting a surface according to an exemplary embodiment, stage moving time may be reduced by moving a stage during scanning, and scanning may be performed a plurality of times for each inspection point by setting unit regions to overlap each other in the inspection object. A representative image may be obtained that has high reliability by averaging images obtained by scanning the inspection points a plurality of times.

Figure 11:
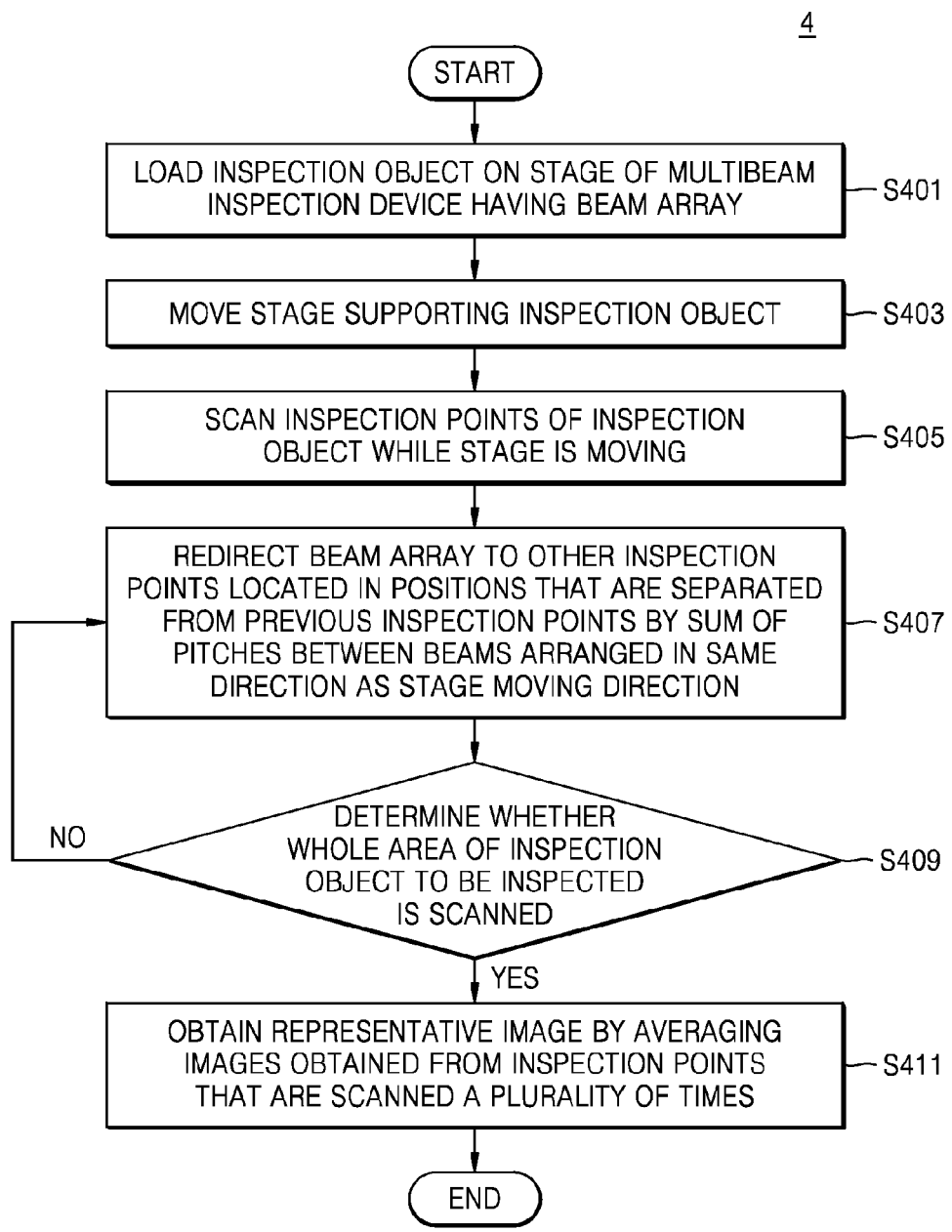
FIG. 11 is a flowchart of a method of inspecting a surface according to another exemplary embodiment.

FIG. 11 is a flowchart of a method 4 of inspecting a surface according to another exemplary embodiment. The method 4 of FIG. 11 is similar to the method 2 of FIGS. 6 to 7D, however, it is different from the surface inspection method 2 in that the scanning is continuously performed a plurality of times on each inspection point of unit regions with an identical beam. The method 4 is also different from the method 3 of FIGS. 8 to 10G in that the scanning is performed a plurality of times on each inspection point of unit regions with different beams. A plurality of images corresponding to an identical inspection point may be used for obtaining a representative image having high reliability through image averaging.

Referring to FIG. 11, first, an inspection object is loaded on a stage of a multibeam inspection device configured to generate a beam array (S401). A stage that supports the inspection object moves (S403). Next, the beam array scans inspection points of any one unit region of the inspection object a plurality of times while the stage is moving (S405). The number of scans may be determined arbitrarily according to inspection conditions. After finishing scanning of the inspection points in the one unit region, the beam array is deflected from the inspection points to other inspection points located at positions separated from the inspection points of the one unit region by a sum of pitches between beams of the one unit region in the same direction as the stage moving direction (S407). After determining whether the whole area of the inspection object to be inspected has been scanned (S409), and when the whole area of the inspection object to be inspected has not yet been scanned, the scanning (S405) and the beam array deflection (S407) may be performed repeatedly. A representative image may be obtained by averaging the images obtained by scanning the inspection points a plurality of times (S411). This will be described in detail with reference to FIGS. 12A to 12F.

FIGS. 12A to 12F are side views of a stage with an inspection object of which inspection points are scanned plural times with corresponding identical beams while the stage is moving, according to the method 4 of inspecting a surface according to an exemplary embodiment.

Referring to FIGS. 12A to 12F, the stage 15 moves in the arrow direction 15$d$ while a first unit region T1 from among a plurality of unit regions is being scanned. For example, the stage moving time may not increase the total inspection time because the stage 15 moves simultaneously while the first unit region T1 is being scanned so that a second unit region T2 may be immediately scanned after scanning the first unit region T1. Accordingly, after finishing the scanning corresponding to the first unit region T1, the scanning corresponding to the second unit region T2 may be performed immediately without any idle time between scans.

Figure 12A:
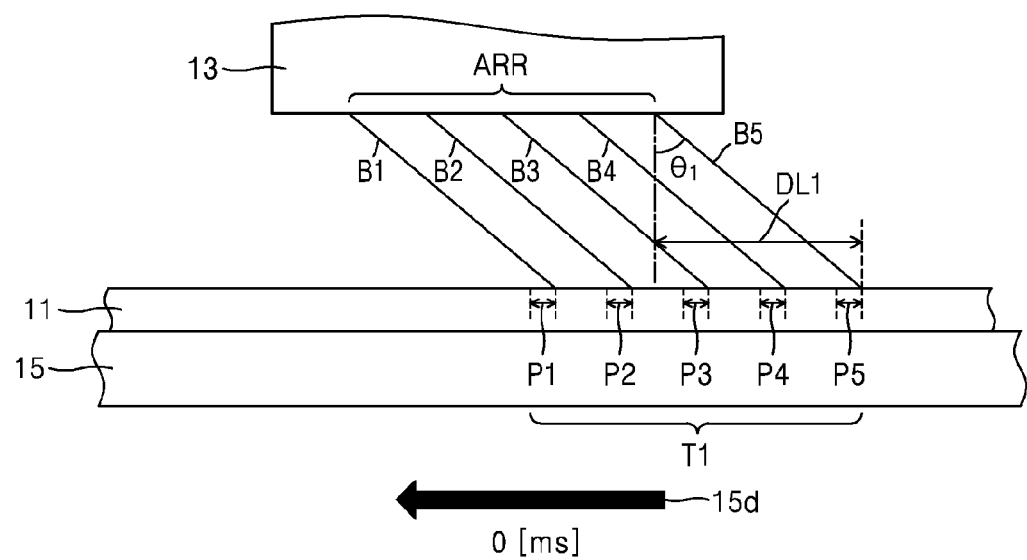
FIGS. 12A to 12F are side views of an inspecting object inspected via the method of inspecting a surface of FIG. 8.
Figure 12B:
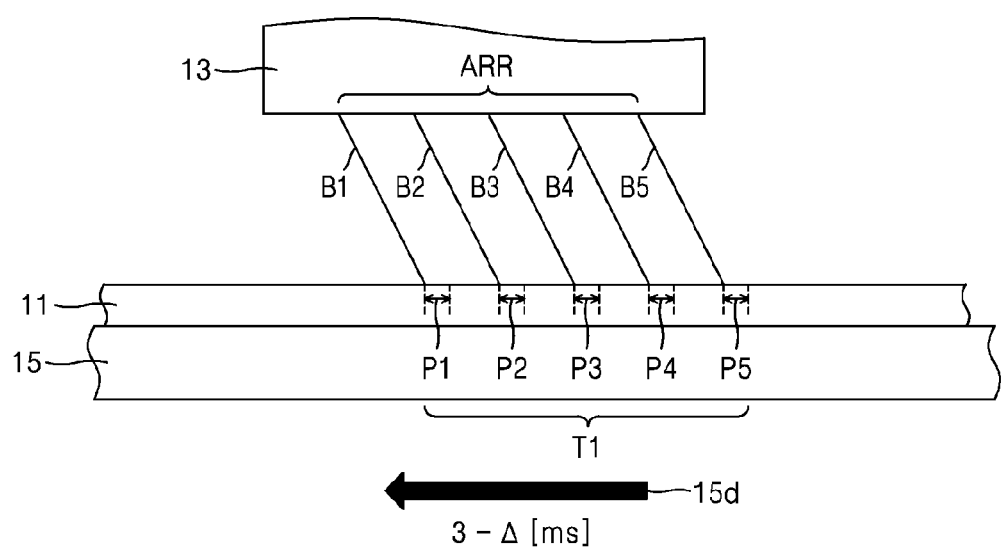

For example, referring to FIGS. 12A and 12B, beams B1 to B5 scan first to fifth inspection points P1 to P5 of the first unit region T1 during a time range from 0 ms to 3−Δms. In this case, the beams B1 to B5 perform scanning along the moving inspection points P1 to P5 while being deflected by a first angle $\theta 1$ at the maximum, for example, by a first deflection distance DL1 at the maximum.

Figure 12C:
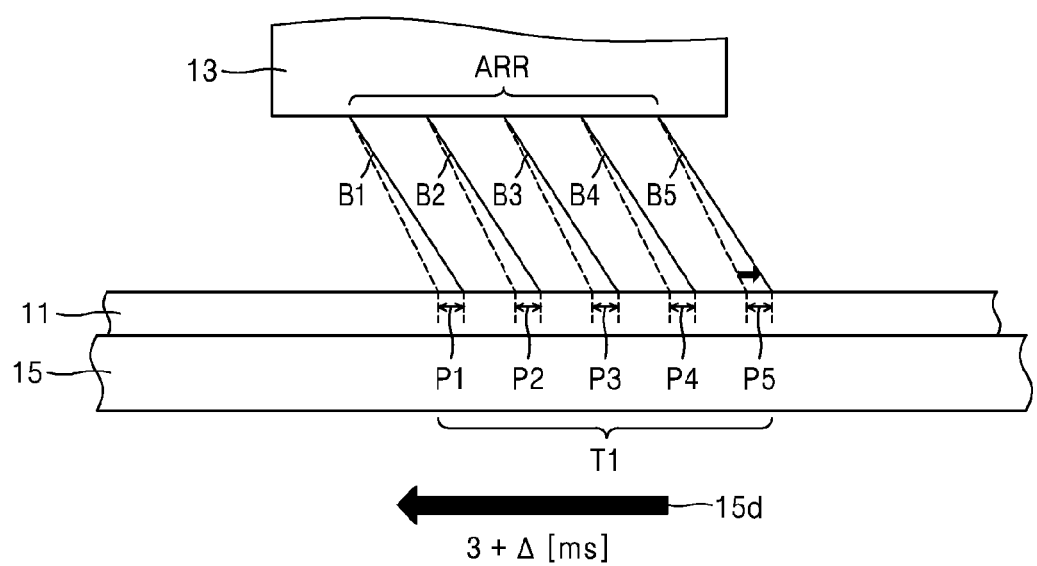

Referring to FIGS. 12B and 12C, a first scanning corresponding to the first to fifth inspection points P1 to P5 of the first unit region T1 is finished at time 3−Δms, which is close to time 3 ms, and thus the beams B1 to B5 may immediately and respectively start a second scanning corresponding to the first to fifth inspection points P1 to P5 at time 3 ms.

Figure 12D:
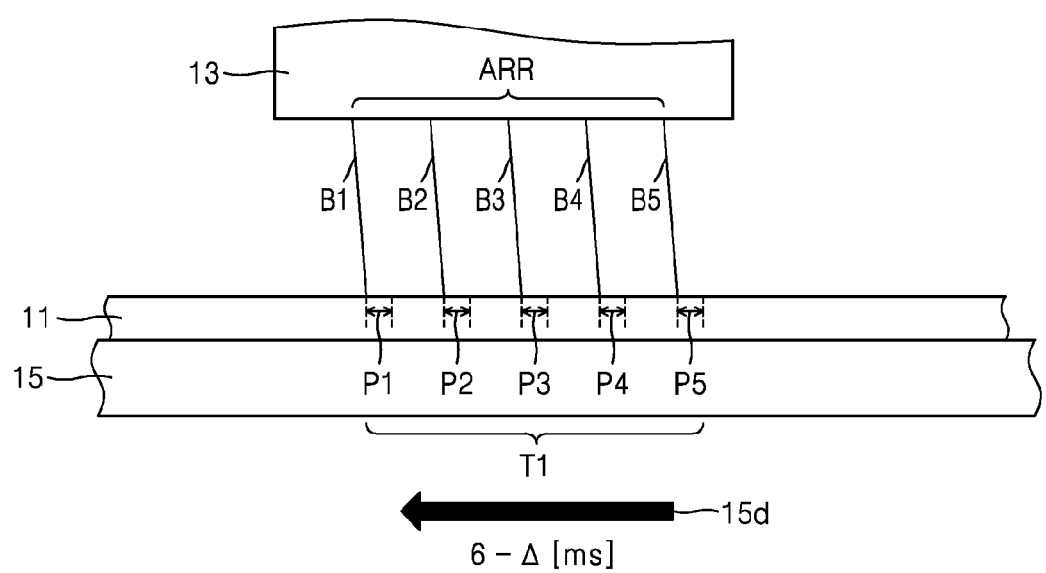

Referring to FIGS. 12C and 12D, the beams B1 to B5 scan twice the first to fifth inspection points P1 to P5 of the first unit region T1 respectively during a time range from 3+Δ ms to 6−Δ ms. A following scanning of the first unit region T1 may be the same as those described with respect to FIGS. 12A to 12D.

Figure 12E:
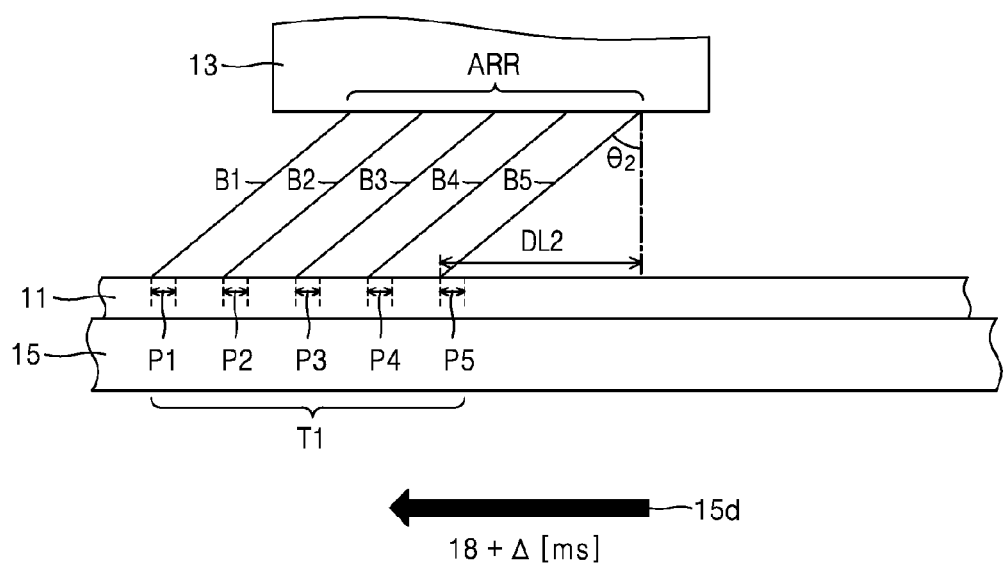
Figure 12F:
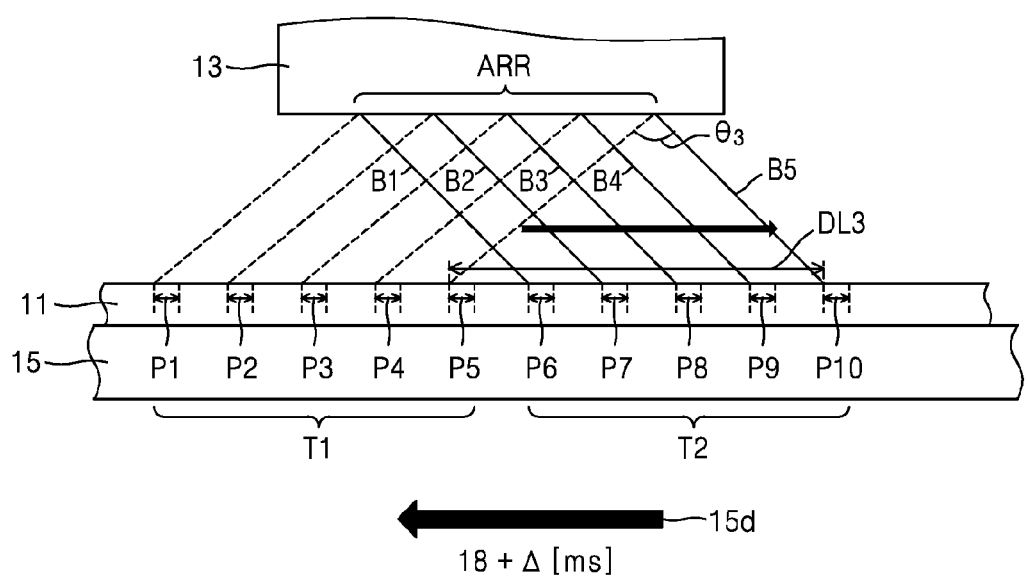

Referring to FIG. 12E, five-time scanning corresponding to the first to fifth inspection points P1 to P5 of the first unit region T1 may be finished at time 15−Δ ms, which is close to time 15 ms. Afterwards, the beams B1 to B5 may be respectively deflected to the sixth to tenth inspection points P6 to P10 of the second unit region T2 with time 15 ms as a start point. The beams B1 to B5 scan during first scanning of the sixth to tenth inspection points P6 to P10 of the second unit region T2 at time 15+Δ ms. A following scanning of another unit region including the second unit region T2 may take place in the same manner as described above with respect to FIGS. 12A to 12E. A plurality of images obtained by scanning each of the inspection points a plurality of times may be used for obtaining a representative image of the inspection points through image averaging. As described herein, Δ may have various values. For example, the Δ in 3+Δ ms may be different from the Δ in 15+Δ ms. For example, if each one is about 0.1% of the time value, they may differ. Alternatively, the values may be the same, for example, a small number such as 0.001 to 0.003 ms.

According to the method 4 of inspecting a surface according to an exemplary embodiment, inspection time may be reduced by moving the stage during scanning, and scanning may be performed a plurality of times for each inspection point by setting repeatedly scanned unit regions in the inspection object. Furthermore, a representative image having high reliability may be obtained through averaging images obtained by scanning each inspection point a plurality of times.

Figure 13:
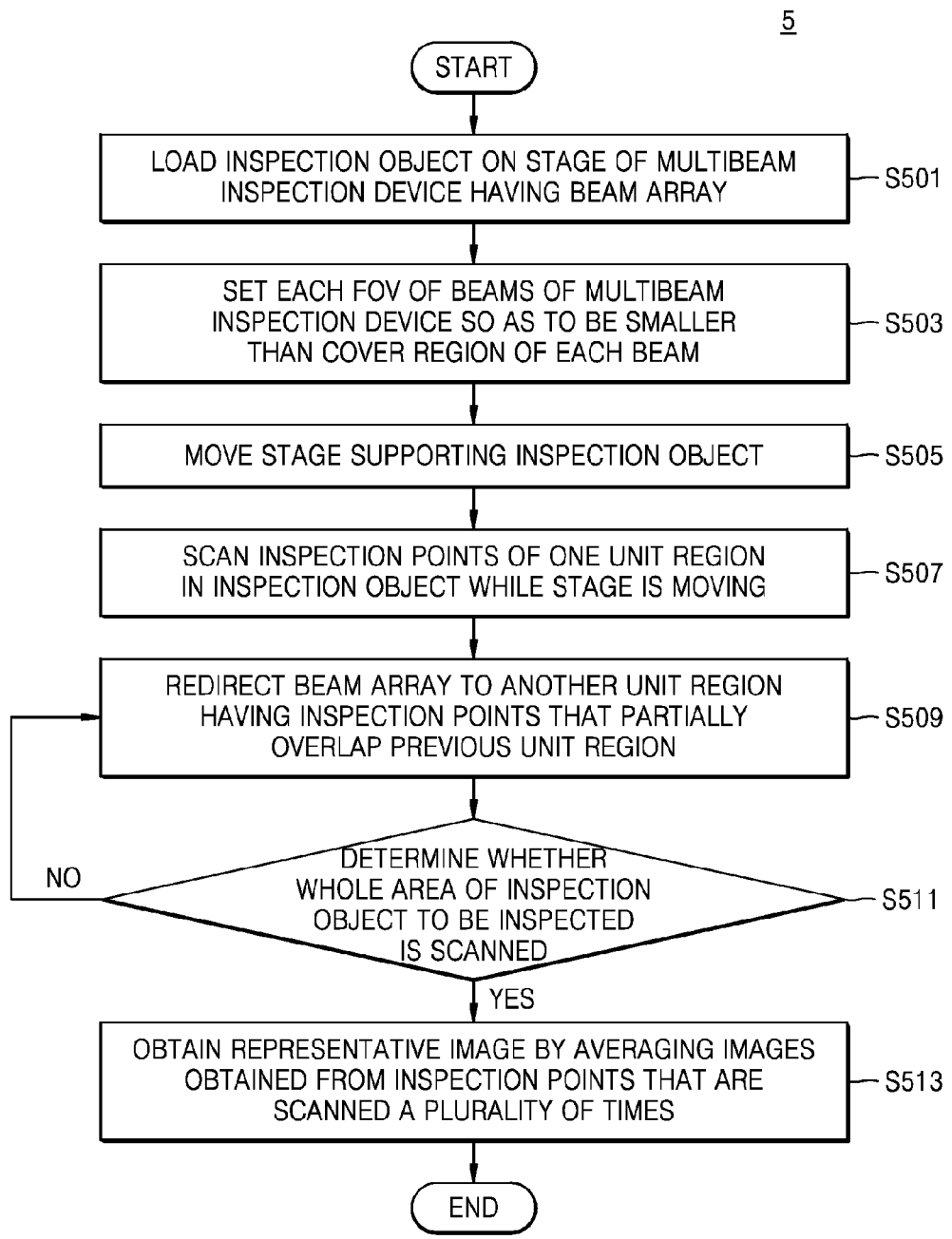
FIG. 13 is a flowchart of a method of inspecting a surface according to another exemplary embodiment.

FIG. 13 is a flowchart of a method 5 of inspecting a surface according to another exemplary embodiment. The method 5 of FIG. 13 may include all of the features of the method 1 of FIGS. 1 to 4, the method 2 of FIGS. 6 to 7D, and the method 3 of inspecting a surface of FIGS. 8 to 10E.

Referring to FIG. 13, an inspection object is loaded on a stage of a multibeam inspection device configured to generate a beam array (S501). Next, an FOV of each of beams included in the beam array may be set to be smaller than a cover region of each of the beams (S503). A stage that supports the inspection object moves (S505). Next, the beam array scans inspection points in any one unit region of the inspection object while the stage is moving (S507). After finishing scanning of the inspection points of the one unit region, the beam array is deflected to another unit region having inspection points that partially overlap the one unit region (S509). For example, the beam array may be deflected to other inspection points located at positions separated from the inspection points of the one unit region by a pitch between the beams. Accordingly, a plurality of images may be obtained by scanning the overlapping inspection points a plurality of times. After determining whether the whole area of the inspection object to be inspected has been scanned (S511), the scanning (S507) and the beam array deflection (S509) may be performed repeatedly until the whole area of the inspection object to be inspected is scanned. A representative image may be obtained by averaging images obtained by scanning the corresponding inspection point a plurality of times (S513).

Figure 14:
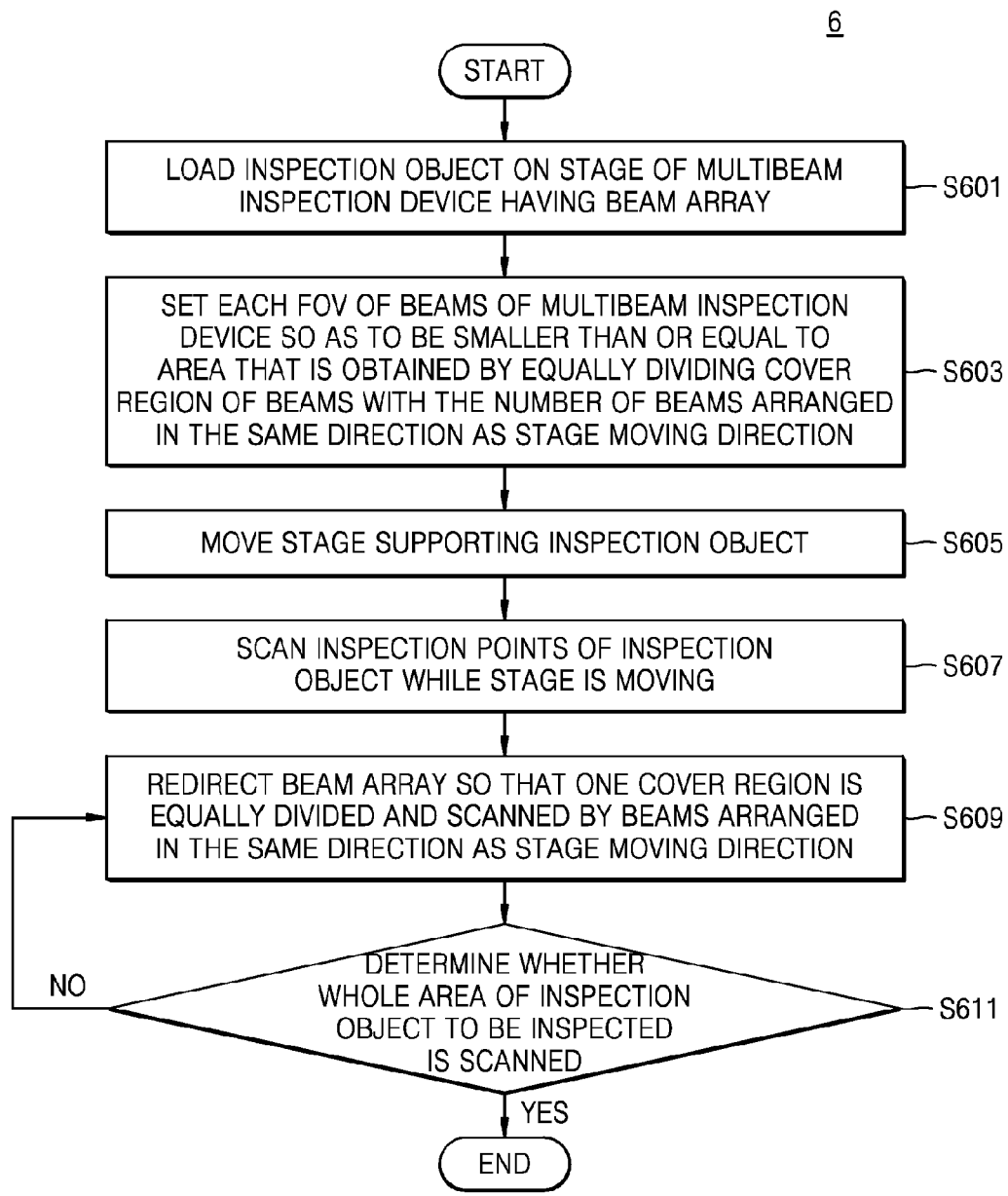
FIG. 14 is a flowchart of a method of inspecting a surface according to another exemplary embodiment.

FIG. 14 is a flowchart of a method 6 of inspecting a surface according to another exemplary embodiment. The method 6 of FIG. 14 is similar to the method 2 of FIGS. 6 to 7D. However, it is different from the method 2 in the deflection of the beam array because a coverage region of an inspection object may be equally divided into a plurality of regions, and each of the divided regions may be scanned by a corresponding beam arranged in the same direction as a stage moving direction.

Referring to FIG. 14, an inspection object is loaded on a stage of a multibeam inspection device configured to generate a beam array (S601). An FOV of each of the beams generated by the multibeam inspection device may be smaller than or equal to an area obtained by equally dividing a cover region of the beams by the number of the beams in the same direction as the stage moving direction (S603). The stage that supports the inspection object moves (S605). Next, the beam array scans a first group of inspection points on the inspection object while the stage is moving (S607). After finishing scanning of the first group of inspection points on the inspection object, the beam array is deflected from the first group of inspection points to a second group of inspection points. In this case, the beam array is deflected so that a region of the inspection object corresponding to any one cover region may be equally divided into a plurality of sub-regions, and each of the sub-regions may be scanned by each of the beams in the same direction as the stage moving direction (S609). For example, when the number of the beams arranged in the same direction as the stage moving direction is five, the region of the inspection object corresponding to any one cover region may be equally divided into five sub-regions, and each of the five sub-regions may be scanned by each of the corresponding five beams. After determining whether the whole area of the inspection object to be inspected has been scanned (S611), the scanning (S607) and the beam array deflection (S609) may be performed repeatedly, for example, until the whole area of the inspection object to be inspected is scanned. This will be described in detail with reference to FIGS. 15A to 15E. In step S609, the first and second groups of inspection points may be referred to as unit regions respectively. For example, the first group of inspection points may be referred to as a first unit region, and the second group of inspection points may be referred to as a second unit region. Similarly, the other groups of inspection points may also be referred to unit regions.

FIGS. 15A to 15E are side views of an inspection object having cover regions, which are equally divided into a plurality of sub-regions, and each of the sub-regions is scanned by each of the corresponding beams arranged in the same direction as a stage moving direction while the stage is moving, according to a method 6 of inspecting a surface according to an exemplary embodiment.

Referring to FIGS. 15A to 15E, an FOV of each of beams B1 to B5 may be smaller than or equal to an area obtained by equally dividing each cover region of the beams B1 to B5 by the number of the beams arranged in the same direction as a moving direction 15d of a stage 15. For example, each width FW of beam inspection points P1a to P9e may be substantially equal to or smaller than the width obtained by equally dividing a width CW of each cover region of the beams by the number of the beams arranged in the same direction as the moving direction 15d. As illustrated in FIGS. 15A to 15E, when five of the beams B1 to B5 are arranged in the same direction as the moving direction 15d of the stage 15, each of the width FW of the beam inspection points P1a to P9e may be substantially equal to or smaller than the width obtained by equally dividing the width CW of each of the cover regions by five.

The stage 15 simultaneously moves during scanning so that the scanning is immediately performed on other inspection points after the current scanning is completed. Accordingly, the total inspection time may not be increased by a moving time of the stage 15.

Figure 15A:
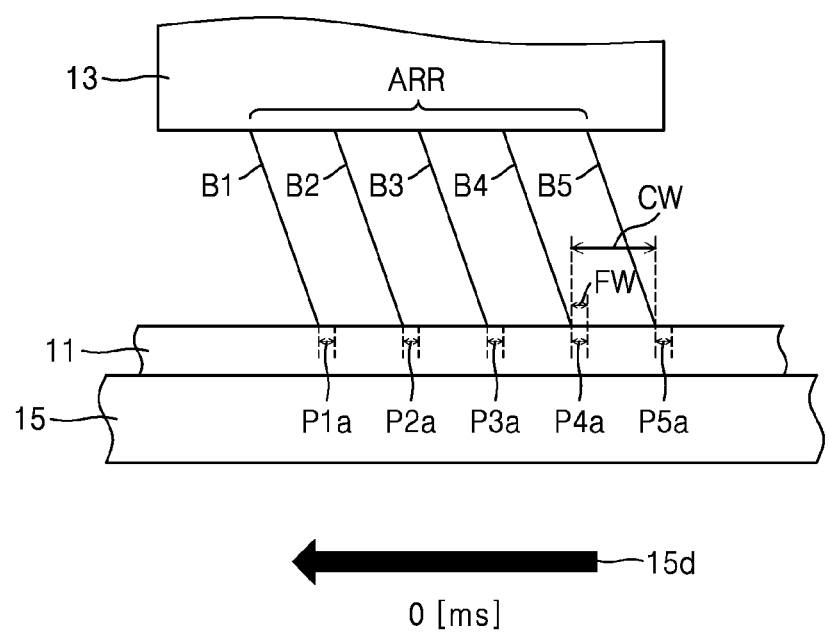
FIGS. 15A to 15E are side views of an inspecting object inspected via the method of inspecting a surface of FIG. 14.
Figure 15B:
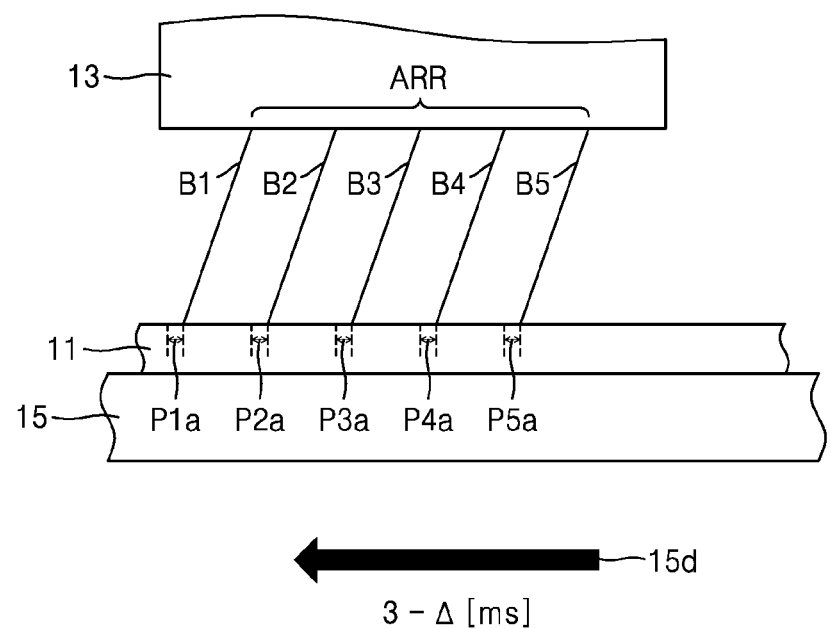

For example, referring to FIGS. 15A and 15B, the beams B1 to B5 scan first inspection points P1a to P5a during a time range from 0 ms to 3−Δ ms.

Figure 15C:
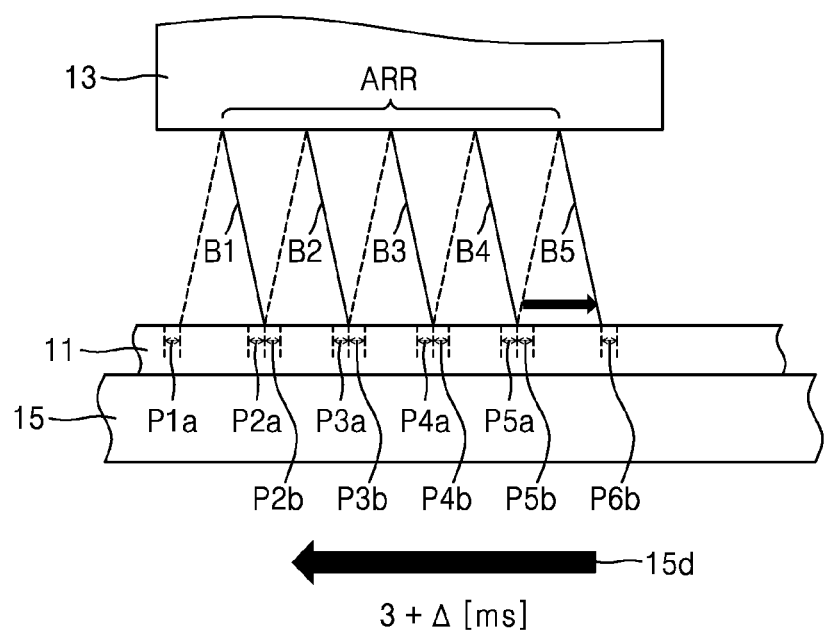

Referring to FIGS. 15B and 15C, scanning the first inspection points P1a to P5a is finished at time 3−Δ ms, which is close to time 3 ms, and thus the beams B1 to B5 may be respectively deflected to second inspection points P2b to P6b adjacent to the first inspection points P1a to P5a at time 3 ms. As described above, the first inspection points P1a to P5a and the second inspection points P2b to P6b are obtained by equally dividing each coverage region of the inspection object 11 defined by a pitch of the beams by the number of the beams in the same direction as the stage moving direction 15d.

Figure 15D:
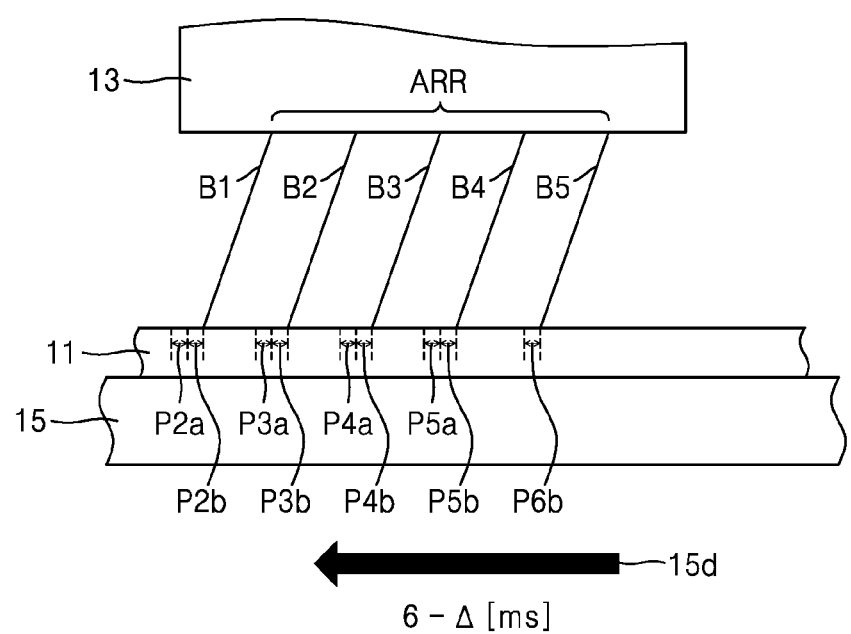

Referring to FIGS. 15C and 15D, the beams B1 to B5 scan the second inspection points P2b to P6b respectively during a time range from 3+Δ ms to 6−Δ ms just after time 3 ms.

In this way, a region of the inspection object 11 corresponding to any one cover region may be equally divided into a plurality of regions, and each of the regions is scanned by the beams B1 to B5 arranged in the same direction as the moving direction 15d of the stage 15 while the stage 15 is moving.

Figure 15E:
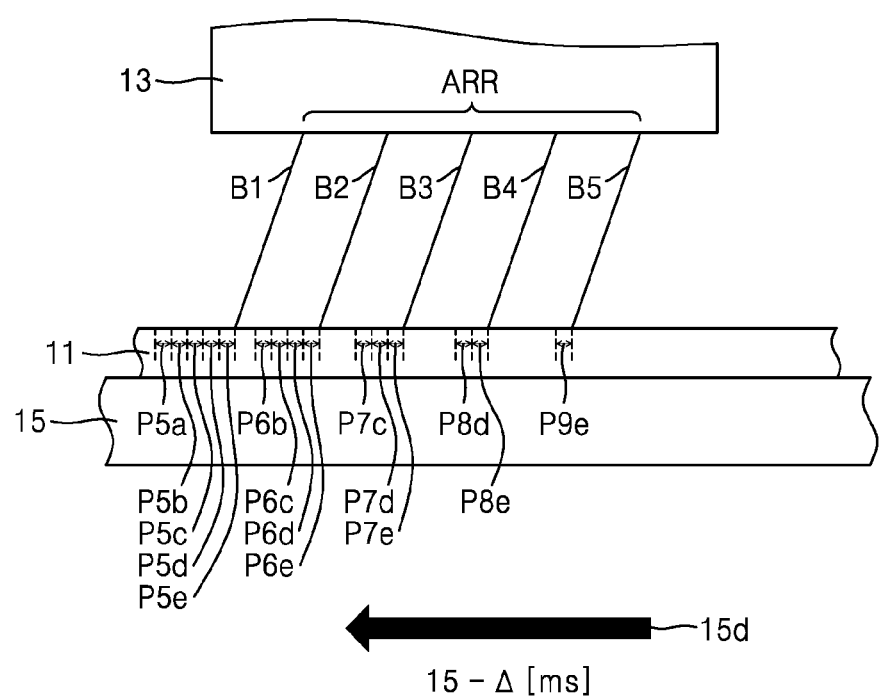

Referring to FIG. 15E, as time 15−Δ ms is approaching, a coverage region of the inspection object 11 defined by a pitch of the beams may be equally divided into a first inspection point P5a, a second inspection point P5b, a third inspection point P5c, a fourth inspection point P5d, and a fifth inspection point P5e, and each of the coverage regions is scanned by the beams B1 to B5. In this case, each deflection distance of the beams B1 to B5 is about 6/5 times of the pitch of the beam, and thus, a multibeam inspection device may be operated in a more stable condition. Furthermore, inspection may be performed over the whole area to be inspected in the inspection object 11 at high speed.

FIGS. 16A to 16E are plan views of a region of an inspection object having cover regions, which are equally divided into a plurality of sub-regions, and each of the sub-regions is scanned by a corresponding beam, according to the method 6 of inspecting a surface of FIGS. 15A to 15E.

Figure 16A:
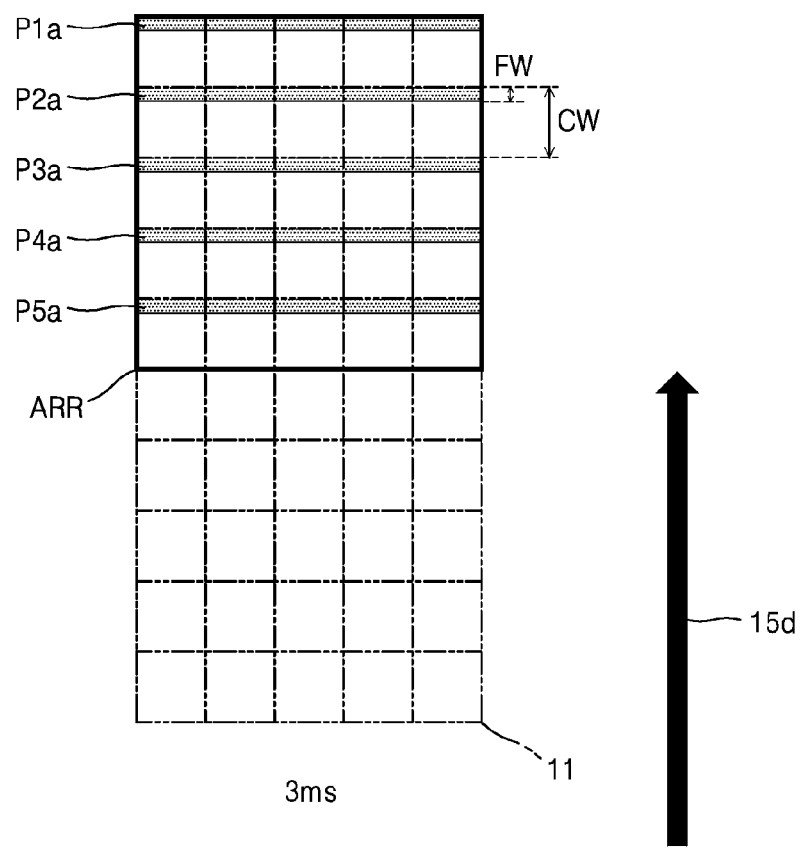
FIGS. 16A to 16E are plan views of an inspecting object inspected via the method of inspecting a surface of FIG. 14.

Referring to FIG. 16A, when five beams are arranged in the same direction as the moving direction 15d of the stage 15, each of the width FW of the first inspection points P1a to P5a that are respectively scanned by the respective beams may be substantially equal to respective width obtained by equally dividing the width CW of each of the cover regions by five. For example, the FOV of each of the beams may be set to be equal to an area obtained by equally dividing each of the cover regions by the number of the beams arranged in the same direction as the moving direction 15d of the stage 15.

In the figures, the FOV of each of the beams is illustrated as being equal to the area obtained by equally dividing each of the cover regions by the number of the beams arranged in the same direction as the moving direction 15d, but the invention is not limited thereto. In some embodiments, the FOV of each of the beams may be smaller than an area obtained by equally dividing the cover region by the number of the beams arranged in the same direction as the moving direction 15d.

Figure 16B:
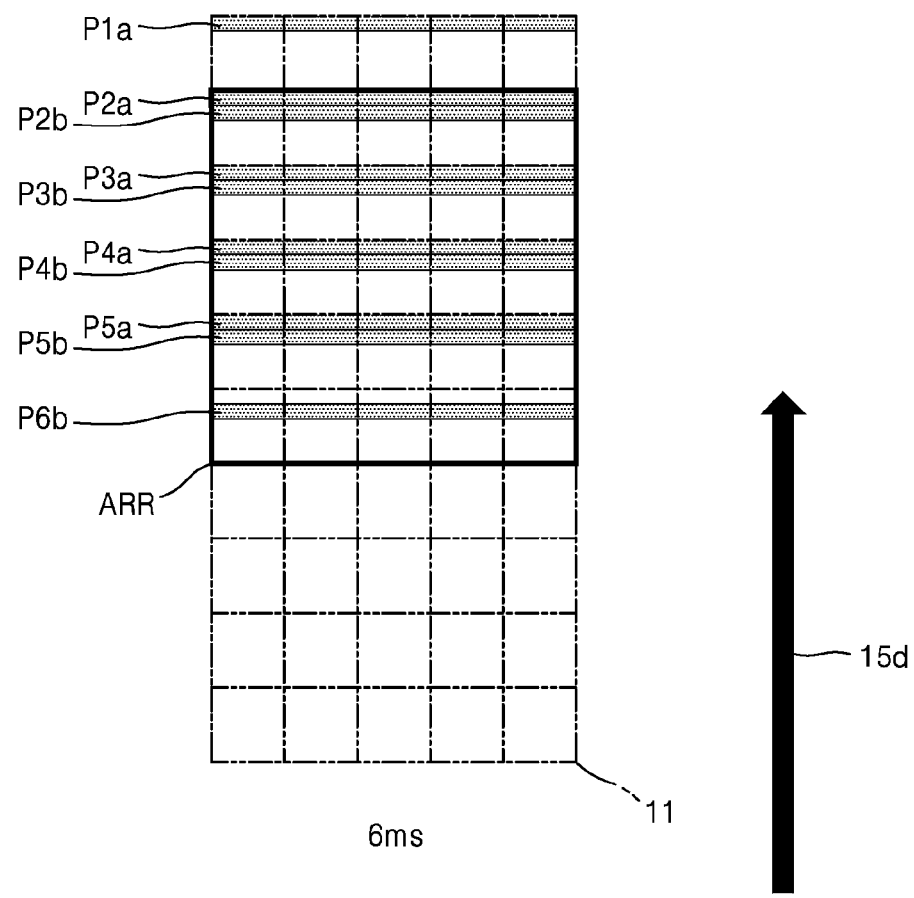

Referring to FIG. 16B, after finishing scanning of the first inspection points P1a to P5a, the beams may scan the second inspection points P2b to P6b adjacent to the first inspection points and each have a ⅕ width of the width CW of each of the cover regions. By repeating this process, the region of the inspection object corresponding to one of the cover regions may be divided and scanned by the beams.

Figure 16C:
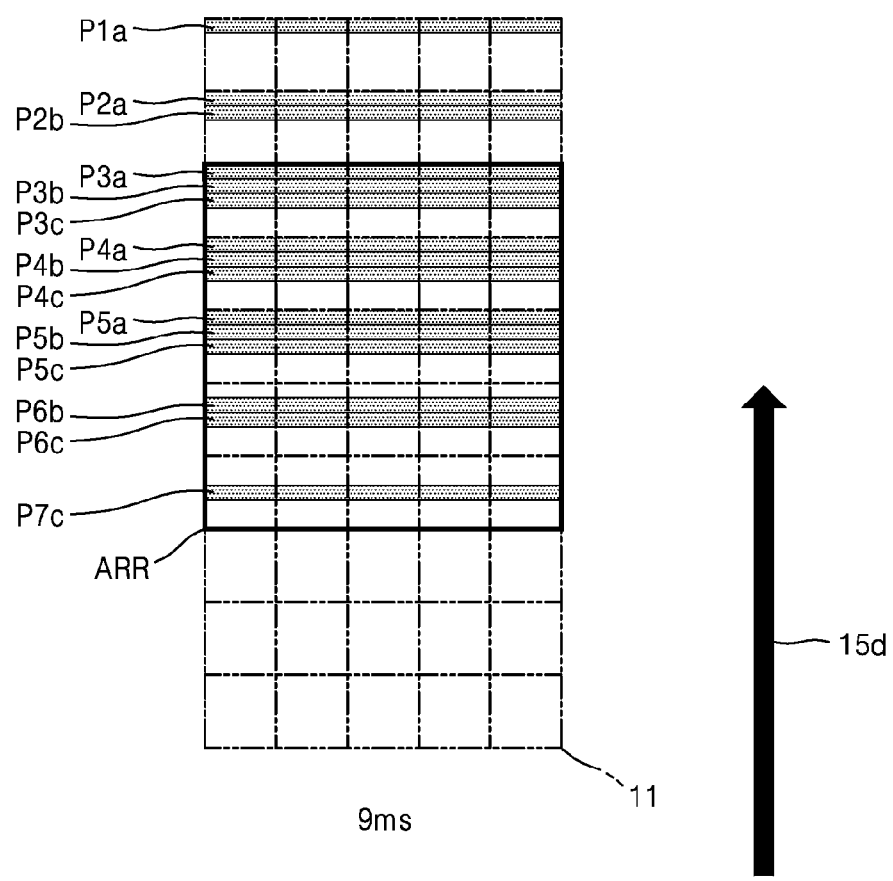
Figure 16D:
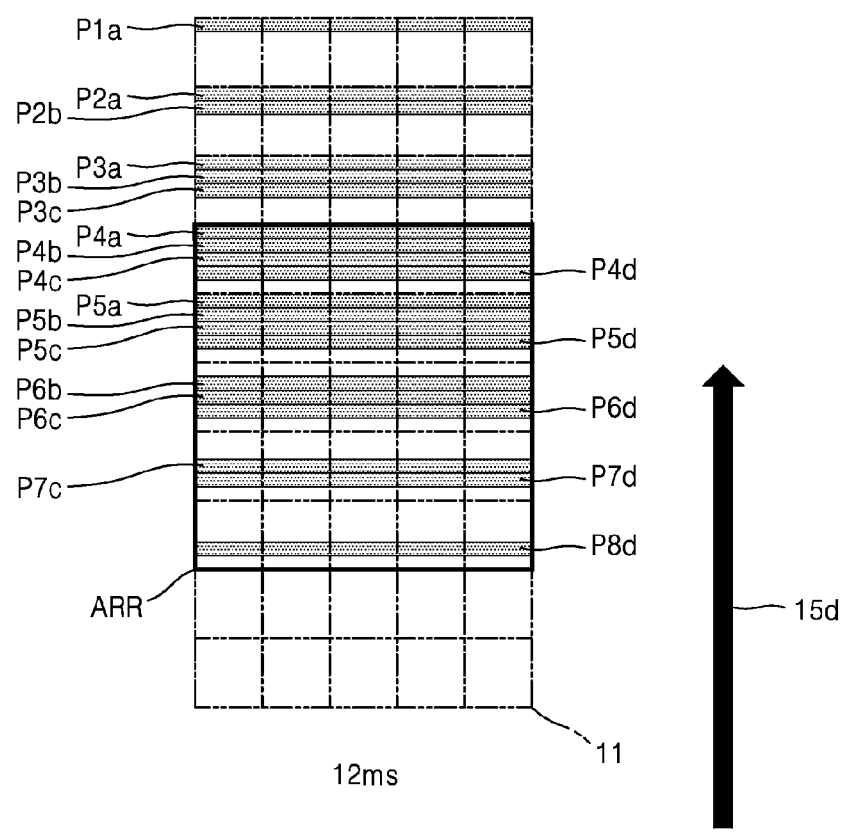
Figure 16E:
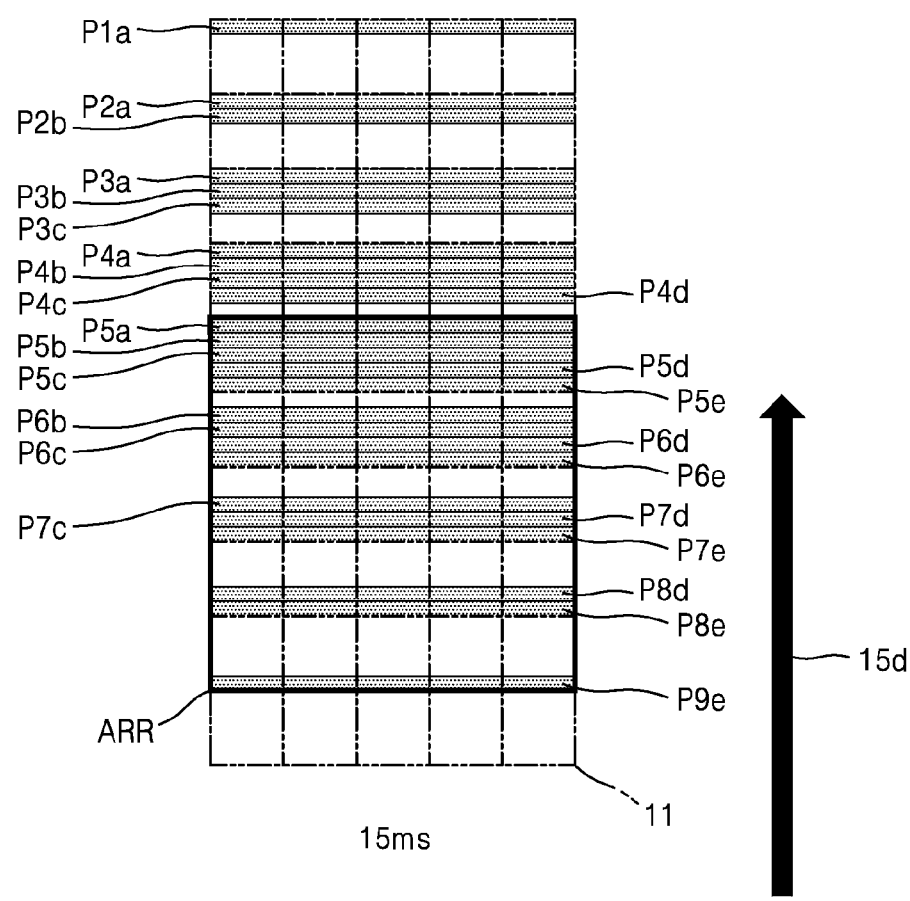

Referring to FIGS. 16C to 16D, as described in FIGS. 16A and 16B, third inspection points P3c to P1c, fourth inspection points P4d to P8d, and fifth inspection points P5e to P9e each having a ⅕ width of the width CW of each of the cover regions may be scanned with corresponding beams. Accordingly, inspection may be performed over the whole area to be inspected in the inspection object 11 at high speed.

According to a method inspecting a surface according to an exemplary embodiment, the FOV F of each of the beams generated by a multibeam inspection device may be set to be smaller than the cover region C. In this case, images of points may be obtained that are located periodically in the whole area of an inspection object with fixed intervals at high speed even though all of the images of the whole area of an inspection object are not obtained. Therefore, a scanning time may be greatly reduced while more accurately predicting the uniformity of the whole area of the inspection object by scanning at relatively high speed the inspection points located over the whole area of the inspection object with fixed intervals.

Furthermore, when a stage movement toward another inspection point is simultaneously performed while scanning any one of the inspection points, the total inspection time may be reduced because the stage moving time is included in the total inspection time.

Furthermore, each inspection point of the inspection object may be scanned a plurality of times with an identical beam or different beams while the stage is moving. A plurality of images obtained by scanning each of the inspection points a plurality of times may be used for obtaining a representative image through image averaging. The representative image may be highly reliable because it is obtained by an average of a plurality of images of the same inspection points.

While the inventive concept has been particularly shown and described with reference to exemplary embodiments thereof, it will be understood that various changes in form and details may be made therein without departing from the spirit and scope of the following claims.

What is claimed is:

1. A method of inspecting a surface, the method comprising:
   loading an inspection object on a stage of a multibeam inspection device configured to generate a beam array;
   setting a plurality of beams in the beam array to respectively have coverage regions defined by respective pitches between the beams;
   setting field of views (FOVs) of the beams to be respectively smaller than the coverage regions; and
   scanning, with the beam array, a plurality of inspection points on the inspection object, the inspection points corresponding to the set FOVs,
   wherein the scanning is performed while the stage that supports the inspection object is moving, and the beam array is redirected along the inspection points on the inspection object moving with the stage.

2. The method of claim 1, wherein the inspection object has a plurality of unit regions, each unit region of the plurality of unit regions corresponding to the beam array, and the beam array is redirected from inspection points of one unit region to inspection points of another unit region.

3. The method of claim 2, wherein the inspection points of the one unit region and the inspection points of the other unit region do not overlap each other.

4. The method of claim 3, wherein each FOV of the beams is smaller than or equal to an area obtained by equally dividing a corresponding coverage region by the number of the beams in the same direction as a stage moving direction.

5. The method of claim 3, wherein a region of the inspection object corresponding to a coverage region of one of the beams is equally divided into a plurality of sub-regions, and each of the sub-regions is scanned by each of the beams in the same direction as a stage moving direction.

6. A method of inspecting a surface, the method comprising:
loading an inspection object on a stage of a multibeam inspection device configured to generate a beam array;
setting a plurality of beams in the beam array to respectively have coverage regions defined by respective pitches between the beams;
setting field of views (FOVs) of the beams to be respectively smaller than the coverage regions; and
scanning, with the beam array, a plurality of inspection points on the inspection object, the inspection points corresponding to the set FOVs,
wherein the scanning is performed while the stage that supports the inspection object is moving, and the beam array is redirected along the inspection points on the inspection object moving with the stage,
wherein the inspection object has a plurality of unit regions corresponding to the beam array, and the beam array is redirected from inspection points of one unit region to inspection points of another unit region,
wherein a redirection distance of the beam array is in a range from a pitch between adjacent beams to a sum of pitches between the beams in the same direction as a stage moving direction.

7. The method of claim 2, wherein at least one of the inspection points of the one unit region and at least one of the inspection points of the other unit region overlap.

8. The method of claim 7, further comprising:
obtaining a representative image by averaging images obtained by scanning the inspection points a plurality of times.

9. The method of claim 2, wherein a redirection distance of the beam array is substantially the same as each of the pitches between the beams.

10. The method of claim 1, wherein the scanning further comprises:
scanning the inspection points on the inspection object a plurality of times and obtaining a representative image by averaging images obtained by scanning the inspection points a plurality of times.

11. The method of claim 1, wherein the scanning covers a whole area of the inspection object.

12. The method of claim 1, wherein the inspection object is a photomask including light shielding patterns.

13. The method of claim 12, further comprising:
measuring a critical dimension (CD) of the light shielding patterns from images obtained by the scanning of the inspection points.

14. A method of inspecting a surface, the method comprising:
loading an inspection object on a stage of a multibeam inspection device configured to generate a beam array;
scanning, with the beam array, inspection areas of a first unit region while the stage is moving, wherein the inspection object includes a plurality of unit regions, each unit region of the plurality of unit regions corresponding to the beam array; and
redirecting the beam array from the inspection areas of the first unit region to inspection areas of a second unit region.

15. The method of claim 14,
wherein an adjacent area of a first inspection area of the first unit region is not scanned with the beam array.

16. The method of claim 15, wherein the first inspection area of the first unit region is smaller than an area formed by a quadrangle connecting respective centers of corresponding four adjacent beams of the beam array,
wherein the sum of the first inspection area of the first unit region and the adjacent area of the first inspection area is substantially the same as the area of the quadrangle.

17. The method of claim 15, wherein the scanning of the inspection areas of the first unit region is performed at a same time with the beam array.

18. The method of claim 15,
wherein the redirecting the beam array is performed after finishing scanning the inspection areas of the first unit region to scan the inspection areas of the second unit region.

19. The method of claim 15, further comprising:
measuring a critical dimension of a pattern from an image obtained by the scanning of a first inspection area.

20. The method of claim 10, wherein the representative image is obtained by averaging images of a same inspection point.

* * * * *